United States Patent
Hosokawa et al.

(10) Patent No.: US 6,797,848 B2
(45) Date of Patent: Sep. 28, 2004

(54) ANTHRACENE DERIVATIVE AND ORGANIC ELECTROLUMINESCENCE DEVICE USING THE DERIVATIVE

(75) Inventors: Chishio Hosokawa, Chiba (JP); Hidetsugu Ikeda, Chiba (JP); Masakazu Funahashi, Chiba (JP)

(73) Assignee: Idemitsu Kosan, Ltd., Tokyo (JP)

( * ) Notice: Subject to any disclaimer, the term of this patent is extended or adjusted under 35 U.S.C. 154(b) by 0 days.

(21) Appl. No.: 10/610,930

(22) Filed: Jul. 2, 2003

(65) Prior Publication Data

US 2004/0100188 A1 May 27, 2004

Related U.S. Application Data

(63) Continuation of application No. 09/818,846, filed on Mar. 28, 2001, now abandoned.

(30) Foreign Application Priority Data

Mar. 29, 2000 (JP) ......................................... 2000/090644
Oct. 19, 2000 (JP) ......................................... 2000/319297

(51) Int. Cl.$^7$ ..................... C07C 13/465; C07C 255/00; C07D 409/00; C07D 213/04
(52) U.S. Cl. ........................... 585/26; 549/59; 546/255; 558/304
(58) Field of Search ............................. 585/26; 549/59; 546/255; 558/304

(56) References Cited

U.S. PATENT DOCUMENTS 5,049,455 A * 9/1991 Uekita et al. ............... 562/496
5,569,800 A * 10/1996 Aruga et al. .................. 585/26
6,399,221 B1 6/2002 Marks et al.

FOREIGN PATENT DOCUMENTS

| JP | 08-012600 | 1/1996 |
| JP | 2000-344691 | 12/2000 |
| JP | 2001-196179 | 7/2001 |

* cited by examiner

*Primary Examiner*—Deborah C. Lambkin
(74) *Attorney, Agent, or Firm*—Oblon, Spivak, McClelland, Maier & Neustadt, P.C.

(57) ABSTRACT

An anthracene derivative represented by general formula (I):

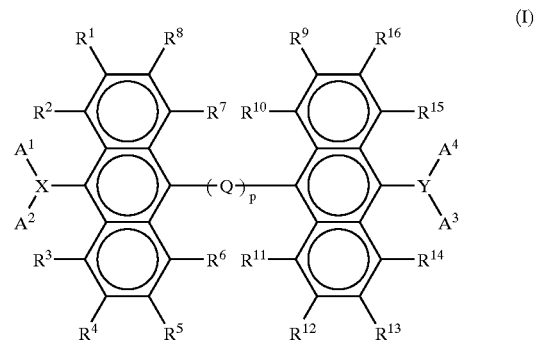

wherein X and Y represent a trifunctional aromatic ring group or the like, $A^1$ to $A^4$ represent an aryl group or a monovalent heterocyclic group, $R^1$ to $R^{16}$ represent hydrogen atom, a halogen atom, cyano group, nitro group, alkyl group or the like, Q represents an arylene group or the like and p represents 0, 1 or 2; and an organic electroluminescence device which comprises at least an organic light emitting layer disposed between a pair of electrodes and the above anthracene derivative. The novel anthracene derivative exhibits a high efficiency of light emission and excellent heat resistance when the derivative is used as a material constituting an organic electroluminescence device.

30 Claims, No Drawings

ANTHRACENE DERIVATIVE AND ORGANIC ELECTROLUMINESCENCE DEVICE USING THE DERIVATIVE

This application is a continuation of application Ser. No. 09/818,846 Filed on Mar. 28, 2001, now abandoned.

TECHNICAL FIELD

The present invention relates to a novel organic compound and an organic electroluminescence (electroluminescence will be referred to as EL, hereinafter) device using the organic compound. More particularly, the present invention relates to an anthracene derivative used as a material constituting an organic EL device and an organic EL device which uses the anthracene derivative and exhibits a high efficiency of light emission and excellent heat resistance.

BACKGROUND ART

Electroluminescence devices which utilize light emission in the electric field show high self-distinguishability because of the self-emission and are excellent in impact resistance because they are completely solid devices. Therefore, organic EL devices are used in the field of the back light of thin film display devices and liquid crystal displays and the planar light source.

EL devices practically used at present are EL devices of the dispersion type. Since EL devices of the dispersion type require an alternating voltage of several tens volts or higher and 10 kiloHerz or higher, driving circuits of the EL devices are complicated.

Therefore, organic EL devices which can be driven at a voltage of 10 volts or lower and can achieve light emission of a high degree are actively studied. For example, organic EL devices having a laminate structure of a transparent electrode/a hole injection layer/a light emitting layer/a back face electrode are proposed (Appl. Phys. Lett., Volume 51, Pages 913 to 915 (1987) and Japanese Patent Application Laid-Open No. Showa 63(1988)-264629). In these organic EL devices, holes are efficiently injected into the light emitting layer through the hole injecting layer disposed in the organic EL devices. The light emitting layer used in the organic EL devices may be a single layer. However, an excellent balance between the electron transporting property and the hole transporting property cannot be achieved by the single layer structure. Improvement in the properties of the organic EL devices has been made by using a multi-layer laminate structure.

Forming a laminate structure causes problems in that the process for producing the organic EL devices is complicated and the time required for the production increases and that restrictions such as the necessity for forming each layer into a sufficiently thin film arise. Moreover, in recent years, a lower driving voltage is required since information instruments are required to have a decrease size and to be portable. Therefore, development of a light emitting material and a hole transporting material which contribute to a decrease in the weight and a decrease in the driving voltage has been conducted. It is known that anthracene can be used as the light emitting material. However, forming a uniform thin film of anthracene is not easy. Therefore, introduction of various substituents into anthracene has been attempted. For example, condensed multi-ring aromatic hydrocarbons are proposed for the light emitting material of organic EL devices (Japanese Patent Application Laid-Open Nos. Heisei 4(1992)-178488, Heisei 6(1994)-228544, Heisei 6(1994)-228545, Heisei 6(1994)-228546, Heisei 6(1994)-228547, Heisei 6(1994)-228548, Heisei 6(1994)-228549, Heisei 8(1996)-311442, Heisei 8(1996)-12600, Heisei 8(1996)-12969 and Heisei 10(1998)-72579).

However, organic EL devices using the above compounds have a problem in that the efficiency of light emission and heat resistance are not sufficient.

DISCLOSURE OF THE INVENTION

The present invention has been made under the above circumstances and has objects of providing a novel compound which exhibits a high efficiency of light emission and excellent heat resistance when the compound is used as a material constituting an organic EL device and an organic EL device using the compound.

As the result of extensive studies by the present inventors to achieve the above objects, it was found that the objects can be achieved by anthracene derivatives having specific structures. The present invention has been completed based on the knowledge.

The present invention can be summarized as follows.

[1] An anthracene derivative represented by general formula (I):

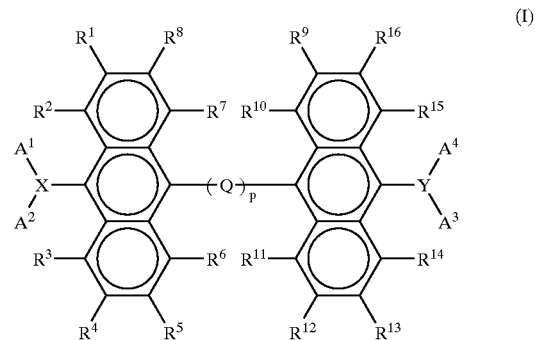

wherein X and Y each independently represent a substituted or unsubstituted trifunctional aromatic ring group having 6 to 30 carbon atoms or a substituted or unsubstituted trifunctional heterocyclic group having 4 to 30 carbon atoms; (1) $A^1$ to $A^4$ each independently represent a substituted or unsubstituted aryl group having 6 to 30 carbon atoms or a substituted or unsubstituted monovalent heterocyclic group having 4 to 30 carbon atoms or (2) $A^1$ represents hydrogen atom, $A^2$ represents a styryl group in which a phenyl portion may be substituted and an α-position or a β-position of a vinyl portion may be substituted with an alkyl group having 1 to 30 carbon atoms, $A^3$ represents hydrogen atom and $A^4$ represents a styryl group in which a phenyl portion may be substituted and an α-position or a β-position of a vinyl portion may be substituted with an alkyl group having 1 to 30 carbon atoms; $R^1$ to $R^{16}$ each independently represent hydrogen atom, a halogen atom, cyano group, nitro group, a substituted or unsubstituted alkyl group, a substituted or unsubstituted alkoxy group, a substituted or unsubstituted aryloxy group, a substituted or unsubstituted alkylthio group, a substituted or unsubstituted arylthio group, a substituted or unsubstituted amino group or a substituted or unsubstituted aryl group; adjacent groups represented by $R^1$ to $R^{16}$ may form rings by forming bonds between each other; Q represents a substituted or unsubstituted cycloalkylene group having 5 to 30 carbon atoms, a substituted or unsubstituted arylene group having 6 to 30 carbon atoms or a substituted or unsubstituted divalent heterocyclic group having 4 to 30 carbon atoms; and p represents a number selected from 0, 1 and 2.

[2] An anthracene derivative represented by general formula (II):

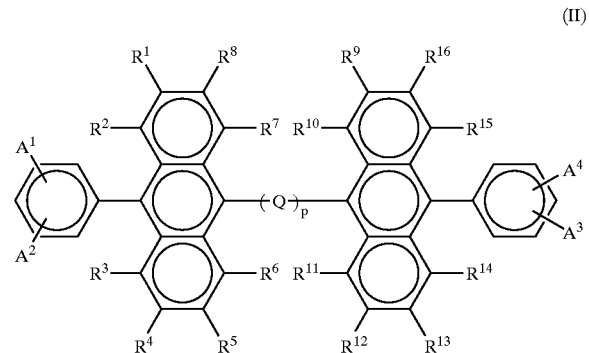

(II)

wherein (1) $A^1$ to $A^4$ each independently represent a substituted or unsubstituted aryl group having 6 to 30 carbon atoms or a substituted or unsubstituted monovalent heterocyclic group having 4 to 30 carbon atoms or (2) $A^1$ represents hydrogen atom, $A^2$ represents styryl group in which a phenyl portion may be substituted and an α-position or a β-position of a vinyl portion may be substituted with an alkyl group having 1 to 30 carbon atoms, $A^3$ represents hydrogen atom and $A^4$ represents a styryl group in which a phenyl portion may be substituted and an α-position or a β-position of a vinyl portion may be substituted with an alkyl group having 1 to 30 carbon atoms; $R^1$ to $R^{16}$ each independently represent hydrogen atom, a halogen atom, cyano group, nitro group, a substituted or unsubstituted alkyl group, a substituted or unsubstituted alkoxy group, a substituted or unsubstituted aryloxy group, a substituted or unsubstituted alkylthio group, a substituted or unsubstituted arylthio group, a substituted or unsubstituted amino group or a substituted or unsubstituted aryl group; adjacent groups represented by $R^1$ to $R^{16}$ may for rings by forming bonds between each other; Q represents a substituted or unsubstituted cycloalkylene group having 5 to 30 carbon atoms, a substituted or unsubstituted arylene group having 6 to 30 carbon atoms or a substituted or unsubstituted divalent heterocyclic group having 4 to 30 carbon atoms; and p represents a number selected from 0, 1 and 2.

[3] An anthracene derivative represented by general formula (II'):

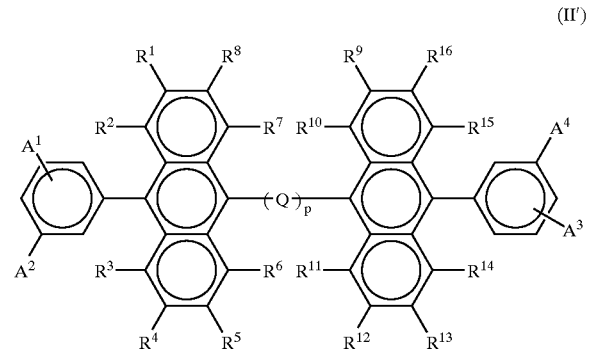

(II')

wherein (1) $A^1$ to $A^4$ each independently represent a substituted or unsubstituted aryl group having 6 to 30 carbon atoms or a substituted or unsubstituted monovalent heterocyclic group having 4 to 30 carbon atoms or (2) $A^1$ represents hydrogen atom, $A^2$ represents a styryl group in which a phenyl portion may be substituted and an α-position or a β-position of a vinyl portion may be substituted with an alkyl group having 1 to 30 carbon atoms, $A^3$ represents hydrogen atom and $A^4$ represents a styryl group in which a phenyl portion may be substituted and an α-position or a β-position of a vinyl portion may be substituted with an alkyl group having 1 to 30 carbon atoms; $R^1$ to $R^{16}$ each independently represent hydrogen atom, a halogen atom, cyano group, nitro group, a substituted or unsubstituted alkyl group, a substituted or unsubstituted alkoxy group, a substituted or unsubstituted aryloxy group, a substituted or unsubstituted alkylthio group, a substituted or unsubstituted arylthio group, a substituted or unsubstituted amino group or a substituted or unsubstituted aryl group; adjacent groups represented by $R^1$ to $R^{16}$ may for rings by forming bonds between each other; Q represents a substituted or unsubstituted cycloalkylene group having 5 to 30 carbon atoms, a substituted or unsubstituted arylene group having 6 to 30 carbon atoms or a substituted or unsubstituted divalent heterocyclic group having 4 to 30 carbon atoms; and p represents a number selected from 0, 1 and 2.

[4] An anthracene derivative represented by general formula (III):

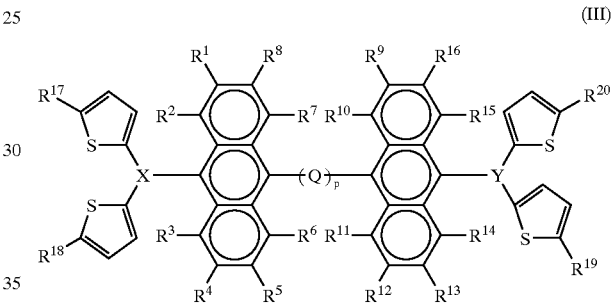

(III)

wherein X and Y each independently represent a substituted or unsubstituted trifunctional aromatic ring group having 6 to 30 carbon atoms or a substituted or unsubstituted trifunctional heterocyclic group having 4 to 30 carbon atoms; $R^1$ to $R^{20}$ each independently represent hydrogen atom, a halogen atom, cyano group, nitro group, a substituted or unsubstituted alkyl group, a substituted or unsubstituted alkoxy group, a substituted or unsubstituted aryloxy group, a substituted or unsubstituted alkylthio group, a substituted or unsubstituted arylthio group, a substituted or unsubstituted amino group or a substituted or unsubstituted aryl group; adjacent groups represented by $R^1$ to $R^{20}$ may for rings by forming bonds between each other; Q represents a substituted or unsubstituted cycloalkylene group having 5 to 30 carbon atoms, a substituted or unsubstituted arylene group having 6 to 30 carbon atoms or a substituted or unsubstituted divalent heterocyclic group having 4 to 30 carbon atoms; and p represents a number selected from 0, 1 and 2.

[5] An organic electroluminescence device which comprises a light emitting area comprising an anthracene derivative described in any of [1] to [4].

[6] An organic electroluminescence device which comprises an organic light emitting layer comprising an anthracene derivative described in any of [1] to [4].

[7] An organic electroluminescence device described in any of [5] and [6], wherein the organic light emitting layer further comprises a substance forming a recombination site.

[8] An organic electroluminescence device described in [7], wherein the substance forming a recombination site is a fluorescent substance having a quantum yield of fluorescence of 0.3 to 1.0.

[9] An organic electroluminescence device described in any of [7] and [8], wherein the substance forming a recombination site is at least one compound selected from styrylamine compounds, quinacridone derivatives, rubrene derivatives, coumarine derivatives, perylene derivatives, pyrane derivatives and fluoranthene derivatives.

[10] An organic electroluminescence.device described in any of [5] to [9], wherein a layer of a chalcogenide, a layer of a metal halide or a layer of a metal oxide is formed between the organic light emitting layer and a cathode or an anode

THE MOST PREFERRED EMBODIMENT TO CARRY OUT THE INVENTION

The organic compound of the present invention is a compound represented by general formula (I):

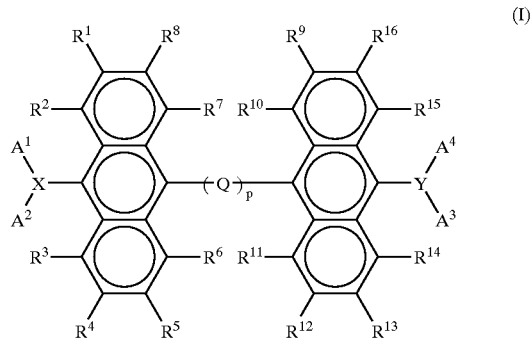

In general formula (I), X and Y each independently represent substituted or unsubstituted trivalent aromatic ring group having 6 to 30 carbon atoms or a substituted or unsubstituted trivalent heterocyclic group having 4 to 30 carbon atoms.

Examples of the trivalent aromatic ring group having 6 to 30 carbon atoms include trivalent groups obtained by eliminating three hydrogen atoms from aromatic compounds such as benzene, naphthalene, biphenyl, terphenyl, triphenyl, chrysene, naphthacene, picene, perylene, pentacene, coronene, rubicene, anthracene, benzo[a]anthracene, benzo[a]pyrene, tetraphenylene and bisanthracene. Examples of the trivalent heterocyclic group having 4 to 30 carbon atoms include trivalent groups obtained by eliminating three hydrogen atoms from heterocyclic compounds such as furan, thiophene, pyrrol, 2-hydroxypyrrol, benzofuran, isobenzofuran, 1-benzothiophene, 2-benzothiophene, indole, isoindole, indolidine, carbazole, 2-hydroxypyrane, 2-hydroxychromene, 1-hydroxy-2-benzopyrane, xanthene, 4-hydroxythiopyrane, pyridine, quinoline, isoquinoline, 4-hydroxyquinolidine, phenanthridine, acridine, oxazole, isoxazole, thiazole, isothiazole, furazane, imidazole, pyrazole, benzimidazole, 1-hydroxyimidazole, 1,8-naphthylidine, pyradine, pyrimidine, pyridazine, quinoxaline, quinazoline, phthaladine, purine, perimidine, 1,10-phenanthroline, thianthrene, phenoxthine, phenoxazine, phenothiazine, phenazine, silacyclopentadiene, silabenzene and dibenzo(b,f)azepine.

In the above general formula (I), (1) $A^1$ to $A^4$ may each independently represent a substituted or unsubstituted aryl group having 6 to 30 carbon atoms or a substituted or unsubstituted monovalent heterocyclic group having 4 to 30 carbon atoms. Examples of the aryl group having 6 to 30 carbon atoms include phenyl group, naphthyl group, biphenyl group, anthranyl group, terphenyl group and styryl group. Examples of the monovalent heterocyclic group having 4 to 30 carbon atoms include monovalent groups corresponding to the trivalent heterocyclic groups described as the examples of the groups represented by X and Y.

In the above general formula (I), (2) $A^1$ and $A^3$ may each represent hydrogen atom and $A^2$ and $A^4$ may each represent a styryl group. The phenyl portion of the styryl group may be substituted and the α-position or the β-position of the vinyl portion of the styryl group may be substituted with an alkyl group having 1 to 30 carbon atoms. When there are a plurality of substituents, the substituents may form a ring structure by forming a bond between each other. Examples of the styryl group include phenylvinylene group, triphenylvinylene group, naphthylvinylene group, biphenylvinylene group, terphenylvinylene group and anthranylvinylene group.

In the above general formula (I), $R^1$ to $R^{16}$ each independently represent hydrogen atom, a halogen atom, cyano group, nitro group, a substituted or unsubstituted alkyl group having 1 to 6 carbon atoms, a substituted or unsubstituted alkoxy group having 1 to 6 carbon atoms, a substituted or unsubstituted aryloxy group having 5 to 18 carbon atoms, a substituted or unsubstituted aralkyloxy group having 7 to 18 carbon atoms, a substituted or unsubstituted alkylthio group having 1 to 20 carbon atoms, a substituted or unsubstituted arylthio group having 6 to 18 carbon atoms, a substituted or unsubstituted amino group, a substituted or unsubstituted ester group having 1 to 6 carbon atoms or a substituted or unsubstituted aryl group having 5 to 16 carbon atoms.

Examples of the alkyl group having 1 to 6 carbon atoms include methyl group, ethyl group, propyl group, isopropyl group, butyl group, isobutyl group, sec-butyl group, tert-butyl group, various types of pentyl groups and various types of hexyl groups. Examples of the alkoxy group having 1 to 6 carbon atoms include methoxy group, ethoxy group, propoxy group, isopropoxy group, butoxy group, isobutoxy group, sec-butoxy group, tert-butoxy group, various types of pentyloxy groups and various types of hexyloxy groups. Examples of the aryloxy group having 5 to 18 carbon atoms include phenoxy group, tolyloxy group and naphthyloxy group. Examples of the aralkyloxy group having 7 to 18 carbon atoms include benzyloxy group, phenetyloxy group and naphthylmethoxy group. Examples of the alkylthio group having 1 to 20 carbon atoms and the arylthio group having 6 to 18 carbon atoms include methylthio group, ethylthio group, phenylthio group and tolylthio group. Examples of the amino group substituted with an aryl group having 5 to 16 carbon atoms include diphenylamino group, dinaphthylamino group and naphthylphenylamio group. Examples of the ester group having 1 to 6 carbon atoms include methoxycarbonyl group, ethoxycarbonyl group, propoxycarbonyl group and isopropoxycarbonyl group. Examples of the halogen atom include fluorine atom, chlorine atom and bromine atom. Adjacent groups represented by $R^1$ to $R^{16}$ may for rings by forming bonds between each other.

In the above general formula (I), Q represents a substituted or unsubstituted cycloalkylene group having 5 to 30 carbon atoms, a substituted or unsubstituted arylene group having 6 to 30 carbon atoms or a substituted or unsubstituted divalent heterocyclic group having 4 to 30 carbon atoms. Examples of the cycloalkylene group having 5 to 30 carbon atoms include cyclopentylene group, cyclohexylene group and cycloheptylene group. Examples of the arylene group having 6 to 30 carbon atoms include phenylene group, naphthylene group, biphenylene group, anthranylene group and terphenylene group. Examples of the divalent heterocyclic group having 4 to 30 carbon atoms include divalent groups corresponding to the trivalent groups described as the examples of the groups represented by X and Y.

In the above general formula (I), p represents a number selected from 0, 1 and 2. When p represents 0, groups at both sides are bonded through a single bond.

When each group in the compounds represented by general formulae (I) to (III) has substituents, examples of the substituents include the groups described as the examples of the groups represented by $R^1$ to $R^{16}$. Similarly to the groups represented by $R^1$ to $R^{16}$, adjacent substituents may for rings by forming bonds between each other.

The anthracene derivative represented by general formula (I) is a compound selected from the compounds having the structures described above. Among the above compounds, compounds having a glass transition temperature of 100° C. or higher are preferable and compounds having a glass transition temperature of 120° C. or higher are more preferable.

The preferred embodiments of the anthracene derivative represented by general formula (I) include anthracene derivatives represented by the following general formulae (II) and (II'):

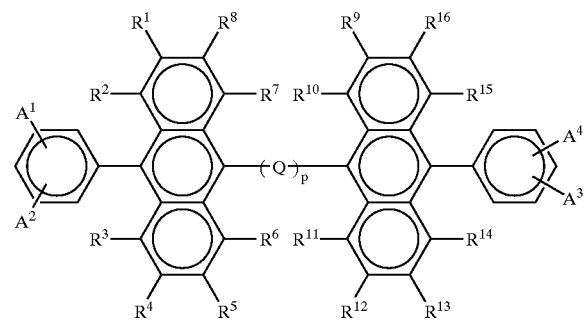

(II)

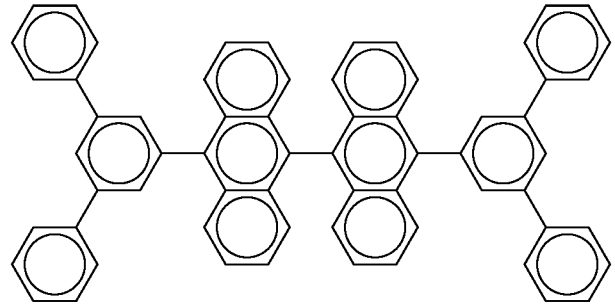

(II')

In the above general formulae (II) and (II'), $A^1$ to $A^4$, $R^1$ to $R^{16}$, Q and p are as defined in general formula (I).

The preferred embodiments of the anthracene derivative represented by general formula (I) further include anthracene derivatives represented by the following general formula (III):

(III)

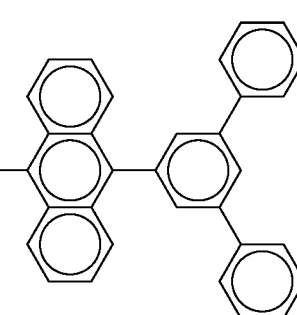

In the above general formula (III), X, Y, Q and p are as defined in general formula (I) and $R^1$ to $R^{20}$ represent the same atoms or groups as those represented by $R^1$ to $R^{16}$.

Adjacent groups represented by $R^1$ to $R^{20}$ may form rings by forming bonds between each other. Adjacent groups represented by $R^1$ to $R^{16}$ frequently form rings by forming bonds between each other.

Examples of the anthracene derivatives represented by general formulae (I), (II), (II') and (III) include compounds E1 to E44 shown in the following:

E1

-continued
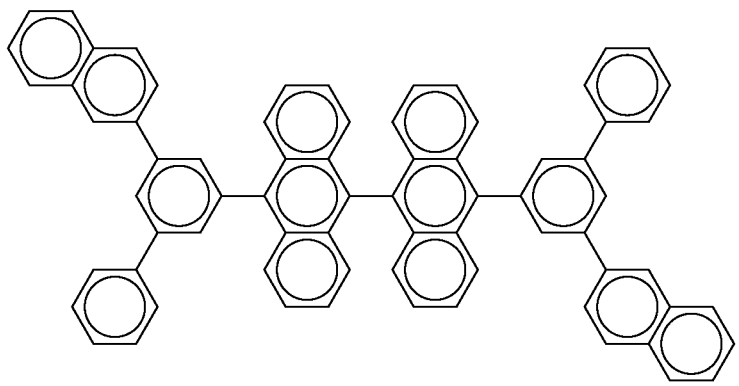
E2
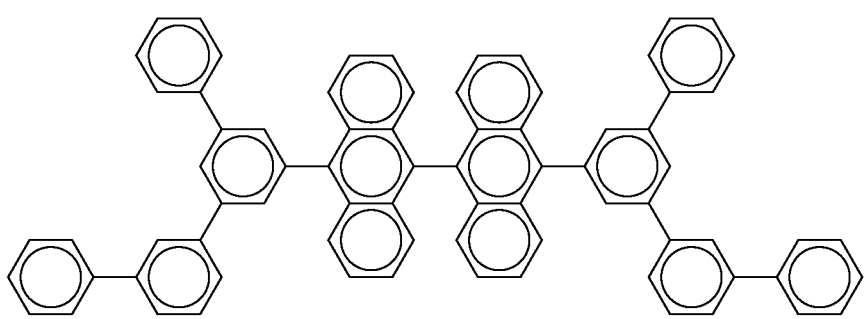
E3
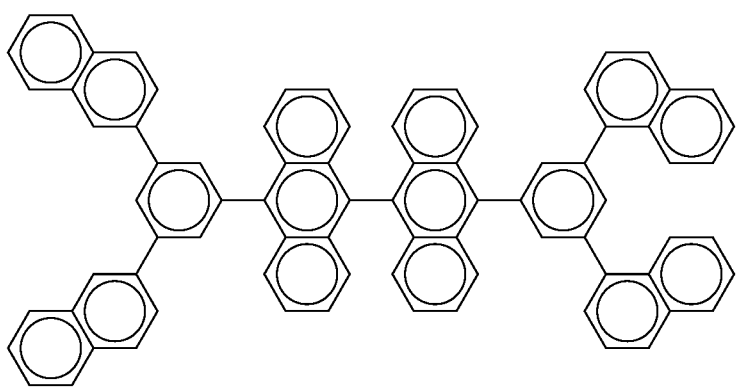
E4
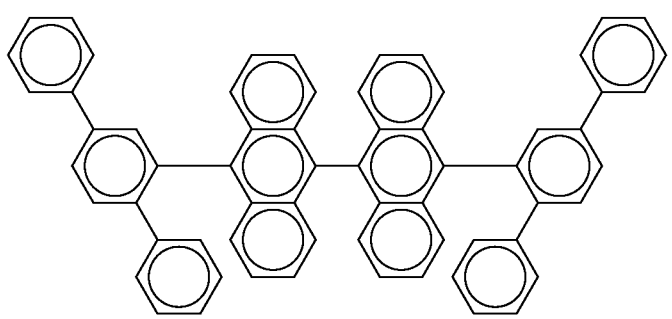
E5

-continued
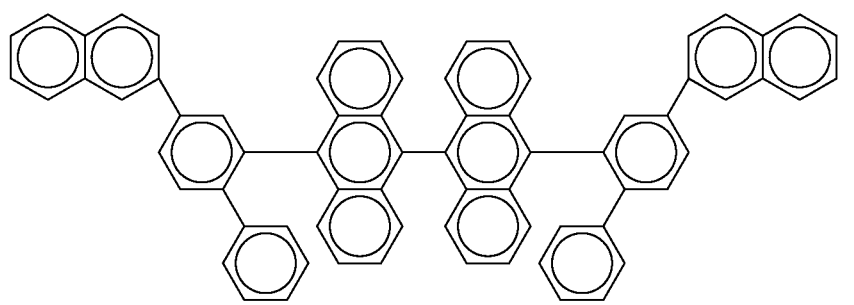
E6
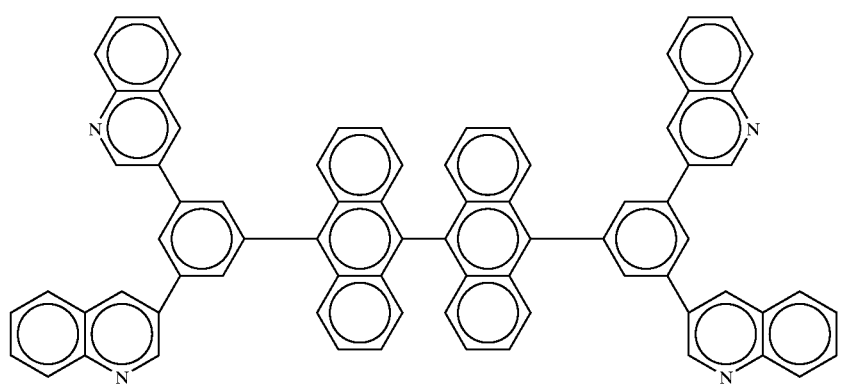
E7
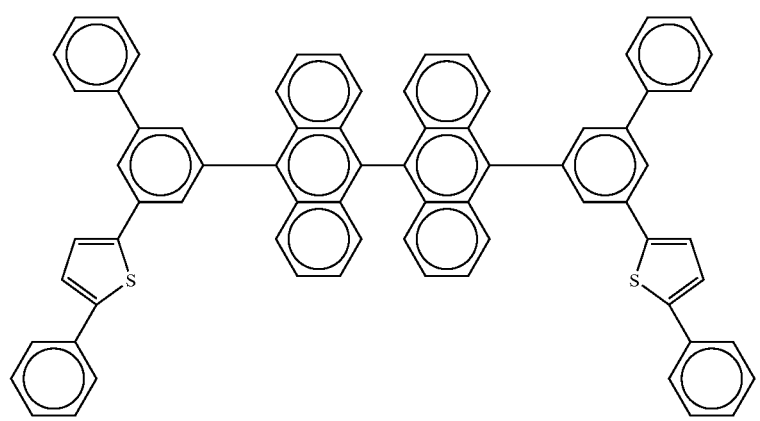
E8
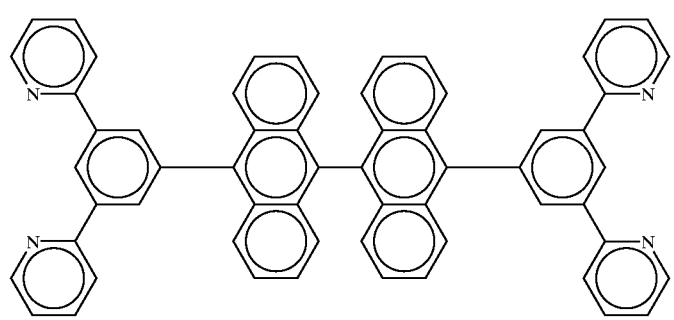
E9

-continued
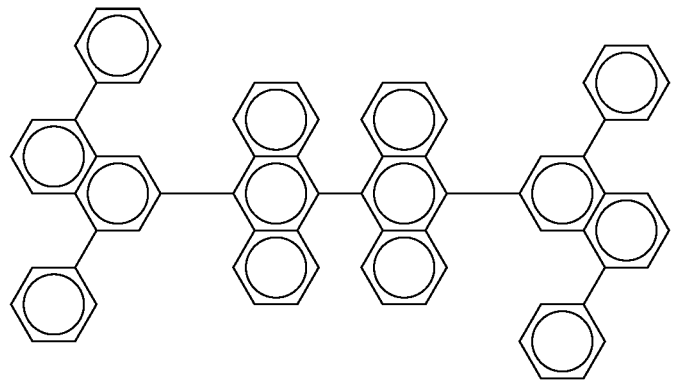
E10
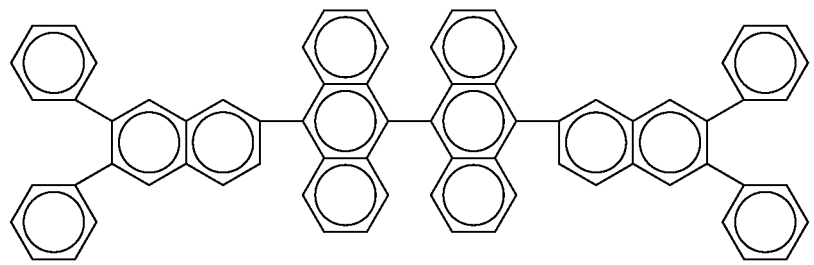
E11
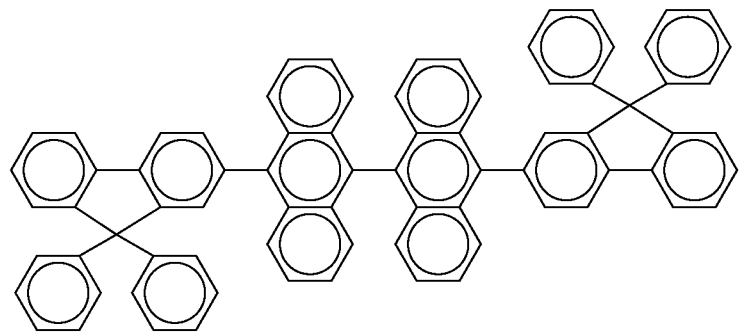
E12
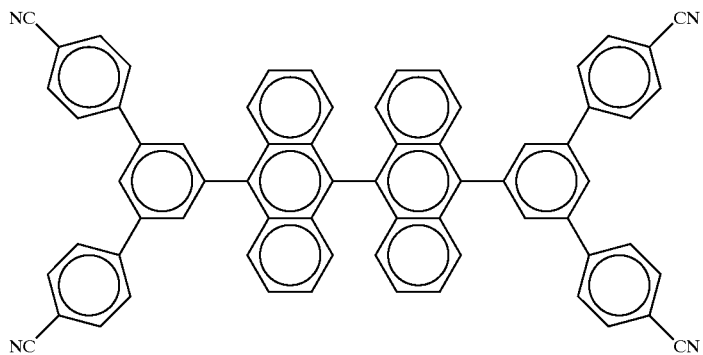
E13

-continued
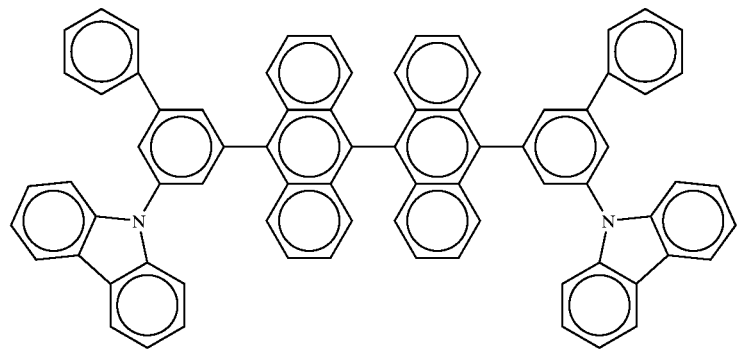
E14
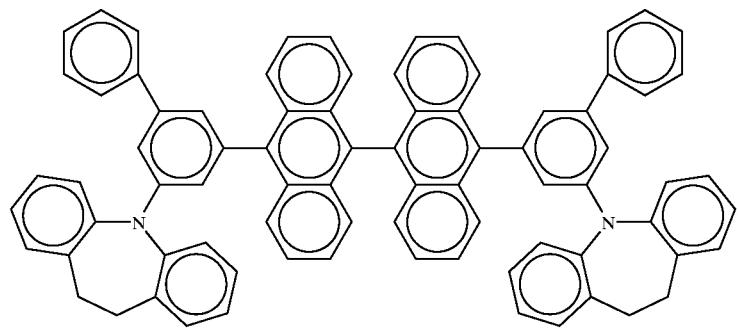
E15
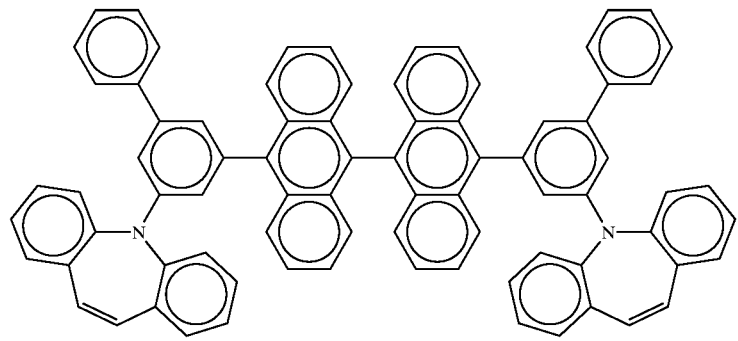
E16
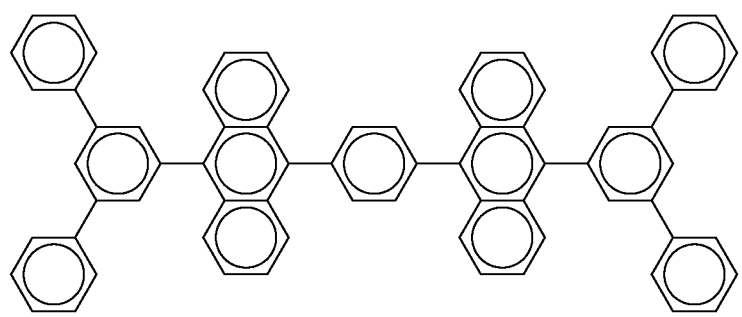
E17

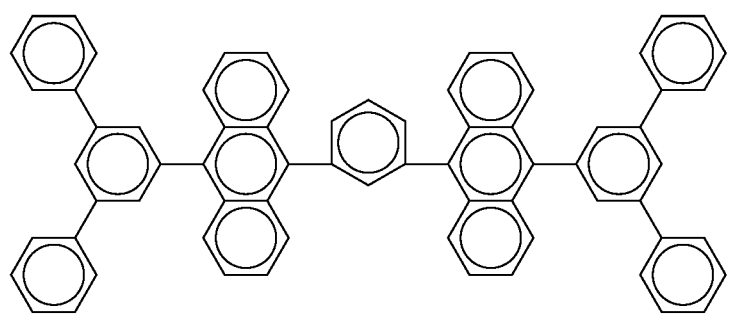
E18
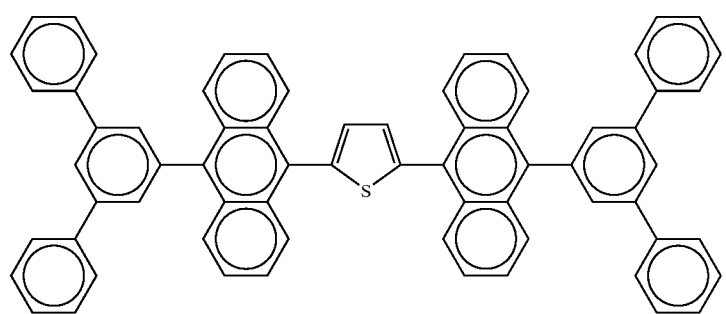
E19
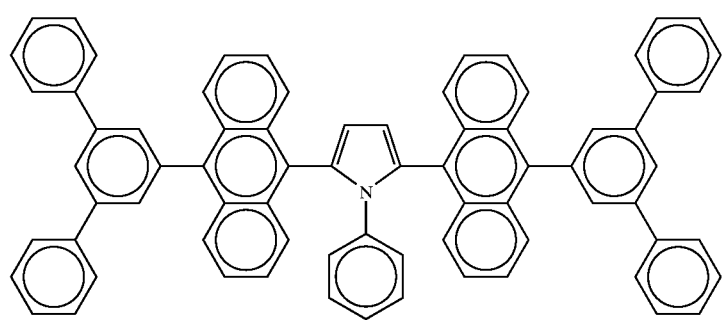
E20
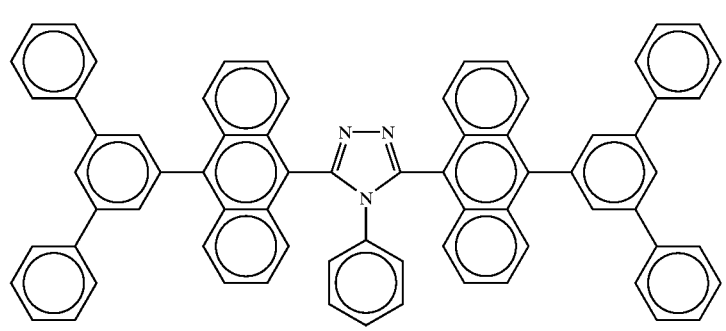
E21
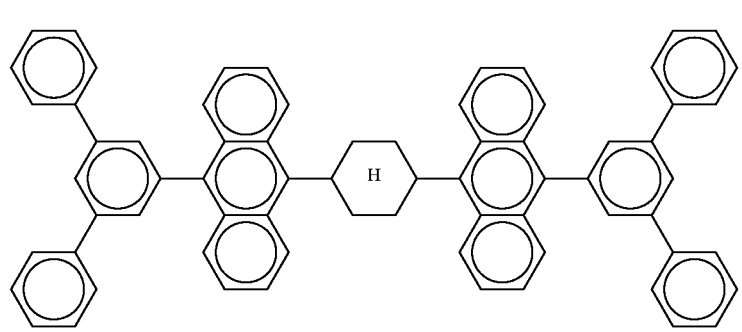
E22

-continued
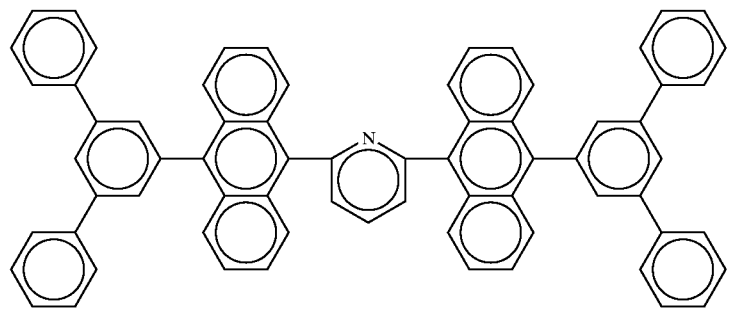
E23
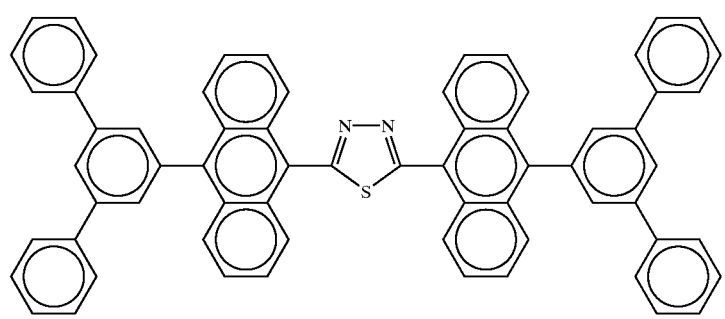
E24
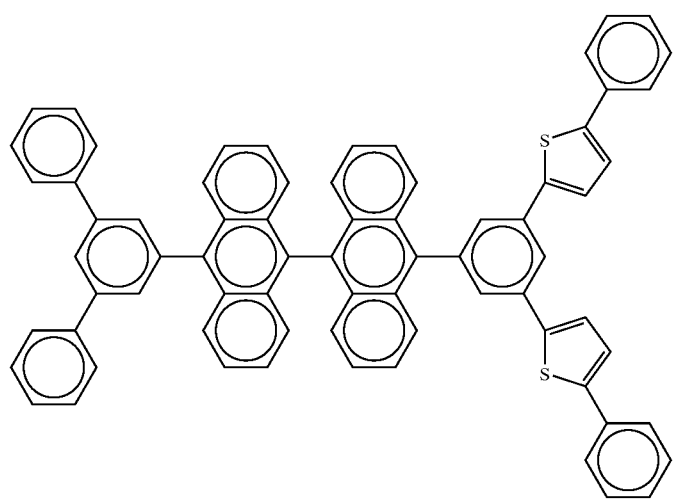
E25
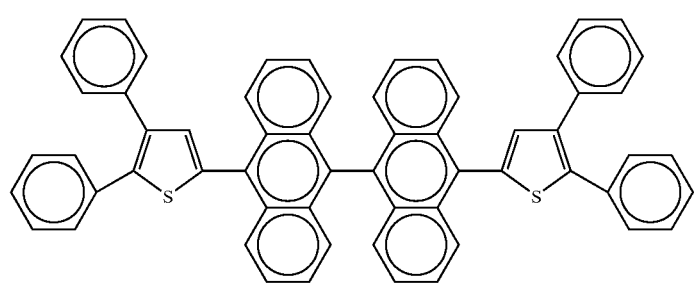
E26

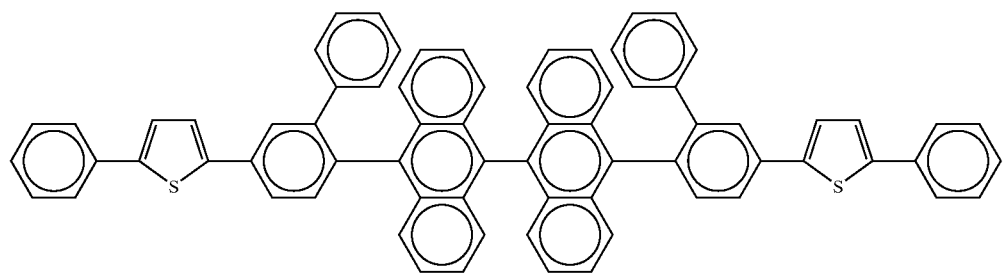
E27
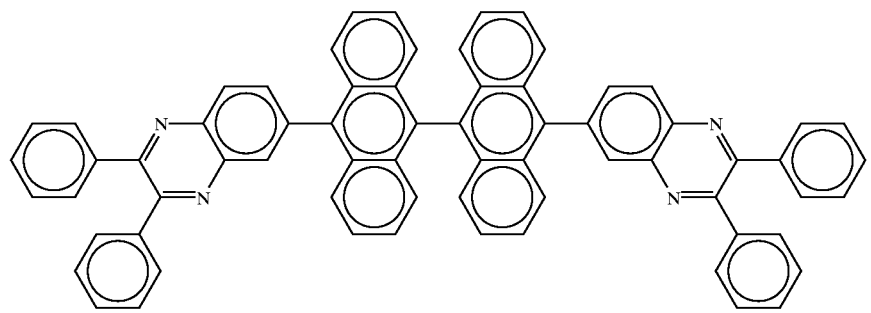
E28
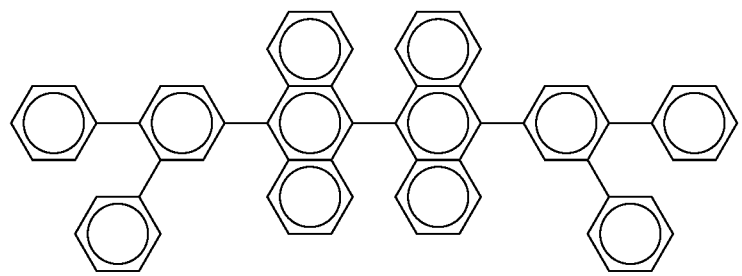
E29
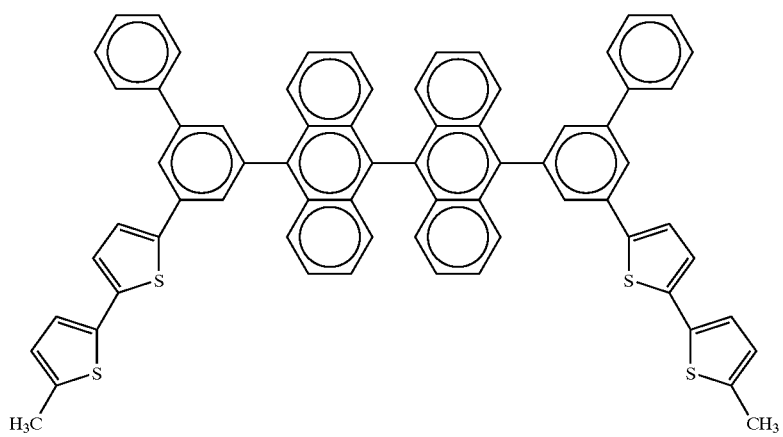
E30

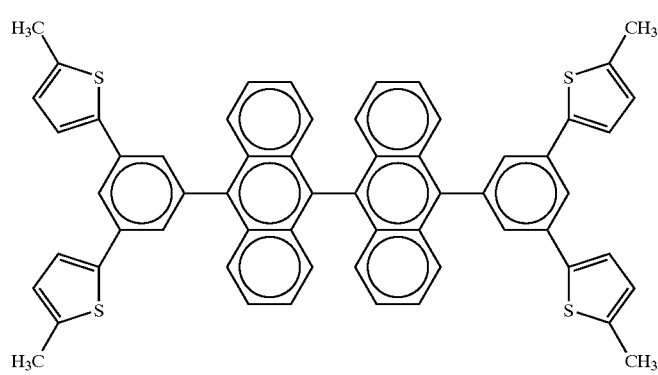
E31
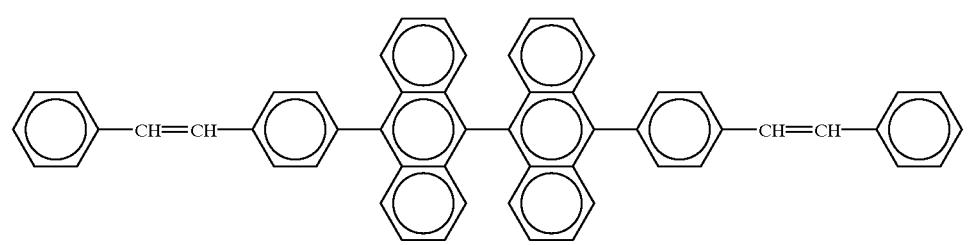
E32
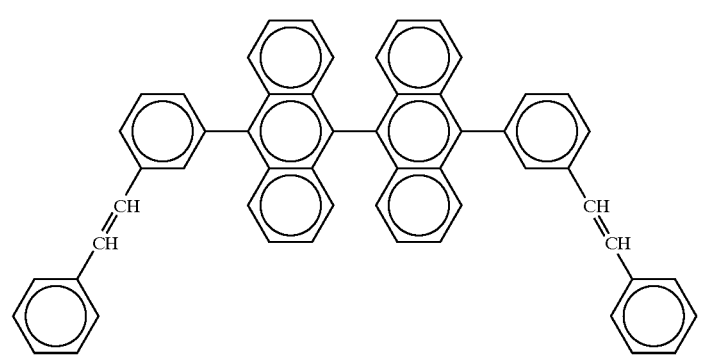
E33
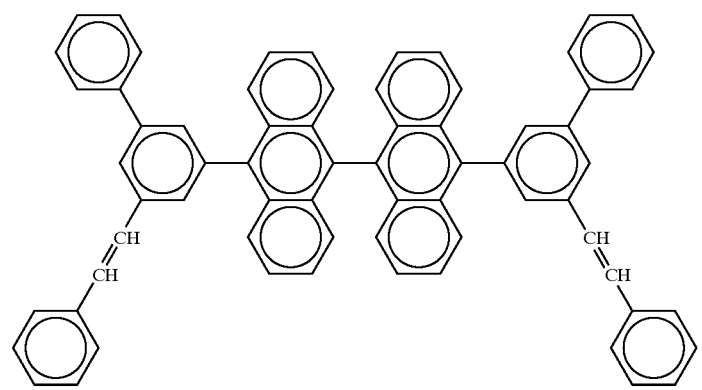
E34

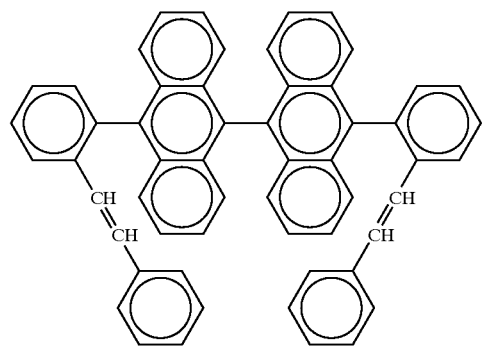
E35
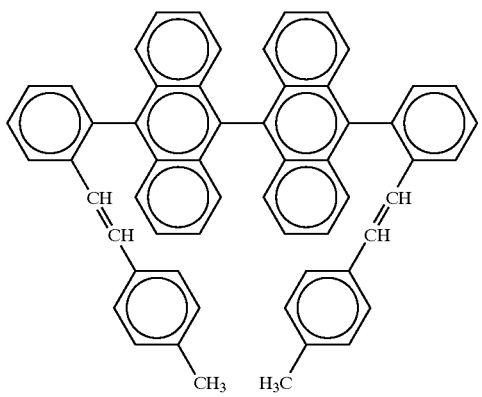
E36
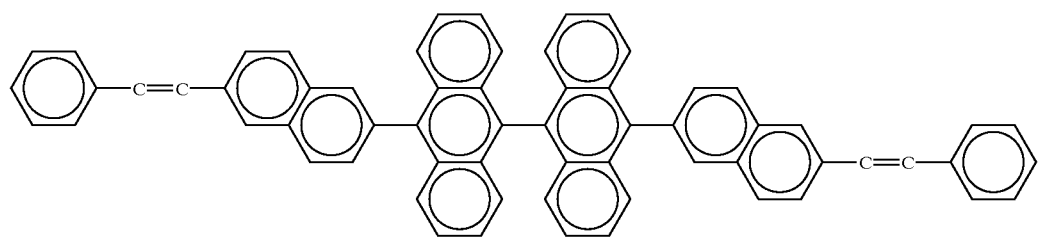
E37
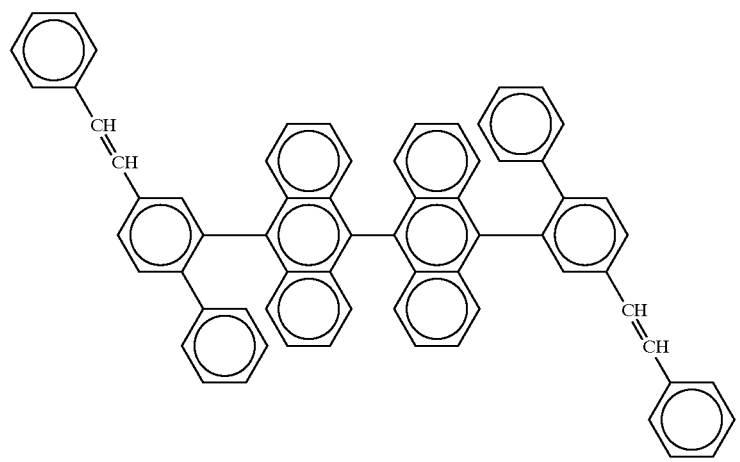
E38
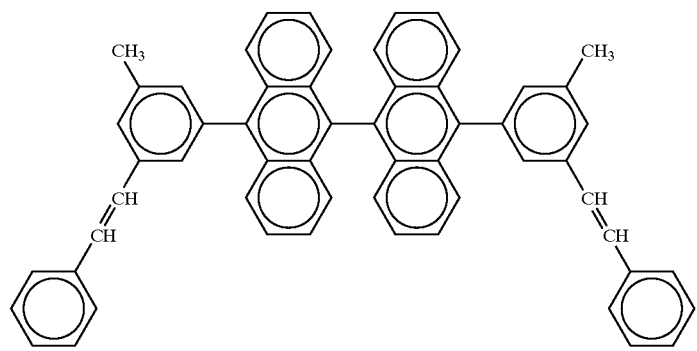
E39

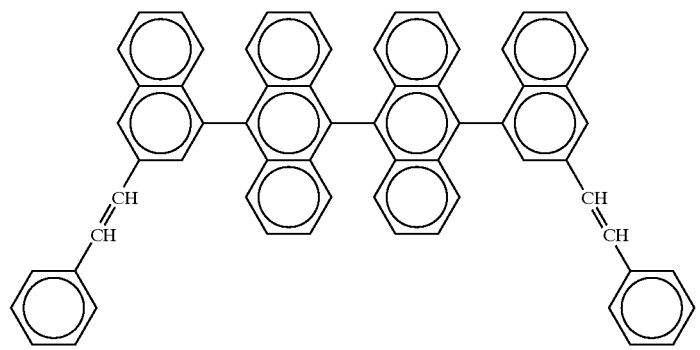
E40
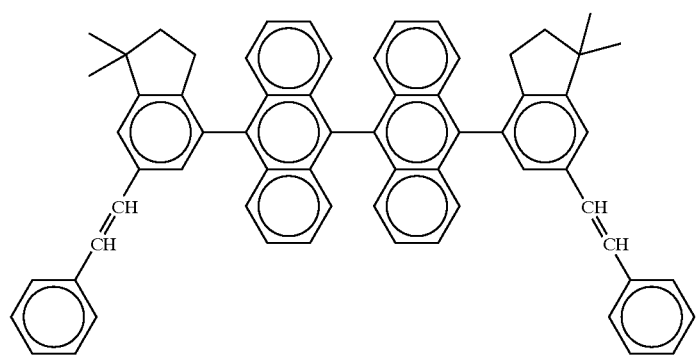
E41
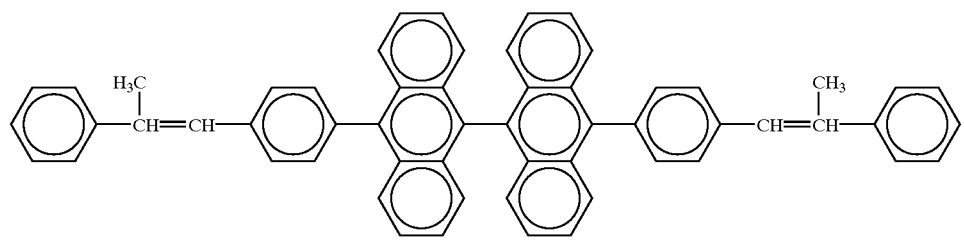
E42
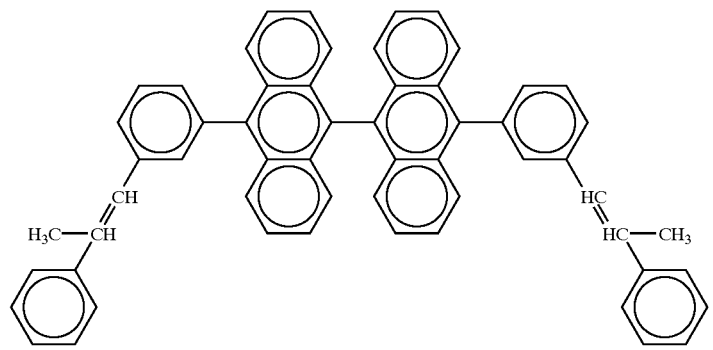
E43

-continued

E44

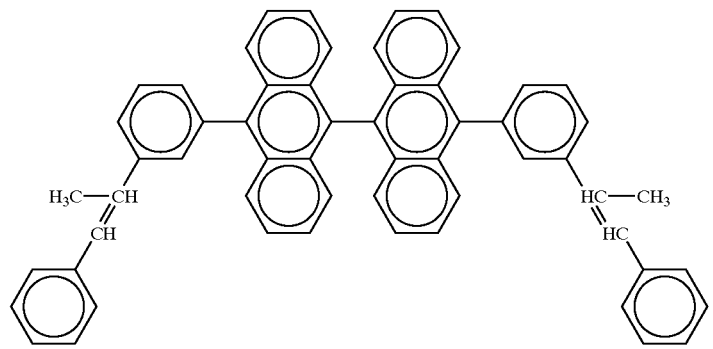

The process for producing the anthracene derivative represented by general formula (I) is not particularly limited and various processes may be used. For example, a desired anthracene derivative can be efficiently produced in accordance with the following process.

The process for producing a compound represented by general formula (I) in which $A^1=A^3$, $A^2=A^4$ and $X=Y$ will be described. A halogen compound represented by general formula (1-a):

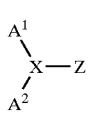

(1-a)

wherein $A^1$, $A^2$ and X are as defined above and Z represents a halogen atom, is reacted with an alkyllithium reagent and converted into a lithium compound. The obtained lithium compound is reacted with a bianthrone compound represented by general formula (1-b):

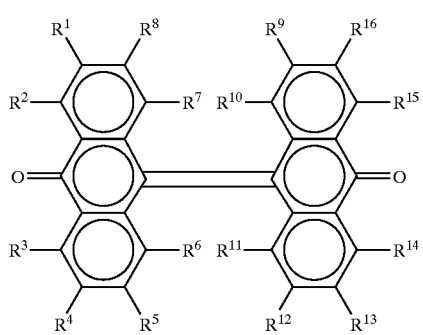

(1-b)

wherein $R^1$ to $R^{16}$ are as defined above, and a bisphenol derivative represented by general formula (1-c):

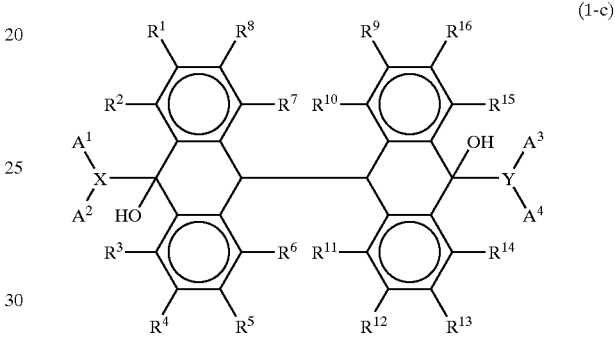

(1-c)

wherein $A^1$, $A^2$ and $R^1$ to $R^{16}$ are as defined above, is obtained. By forming aromatic rings from the bisphenol derivative in accordance with a conventional process, the anthracene derivative represented by general formula (I) can be obtained.

The organic EL device of the present invention is a device having at least an organic light emitting layer disposed between a pair of electrodes. Examples of the construction of the organic EL device include the following constructions:

(1) An anode/a light emitting layer/a cathode;
(2) An anode/a hole injecting layer/a light emitting layer/a cathode;
(3) An anode/a light emitting layer/an electron injecting layer/a cathode;
(4) An anode/a hole injecting layer/a light emitting layer/an electron injecting layer/a cathode;
(5) An anode/an organic semiconductor layer/a light emitting layer/a cathode;
(6) An anode/an organic semiconductor layer/an electron barrier layer/a light emitting layer/a cathode;
(7) An anode/an organic semiconductor layer/a light emitting layer/an adhesion improving layer/a cathode; and
(8) An anode/a hole injecting layer/a hole transporting layer/a light emitting layer/an electron injecting layer/a cathode.

However, the construction of the organic EL device is not limited to the above examples.

Among the above constructions, construction (8) is preferably used. It is preferable that the anthracene derivative represented by any of general formulae (I), (II), (II') and (III) is comprises in the light emitting area such as the light emitting layer, the hole transporting layer, the electron injection layer or the hole injection layer (the layers other than the electrode layers) in the above constructions. It is more preferable that the anthracene derivative is comprised in the light emitting layer.

In general, the organic EL device is prepared on a substrate which transmits light. The substrate which transmits light is the substrate which supports the organic EL device. It is preferable that the substrate which transmits light has a transmittance of light of 50% or greater in the visible region of 400 to 700 nm. It is also preferable that a flat and smooth substrate is used.

As the substrate which transmits light, glass plates and synthetic resin plates are advantageously used. Specific examples of the glass plates include plates made of soda ash glass, glass containing barium and strontium, lead glass, aluminosilicate glass, borosilicate glass, barium borosilicate glass and quartz. Specific examples of the synthetic resin plates include plates made of polycarbonate resins, acrylic resins, polyethylene terephthalate resins, polyether sulfide resins and polysulfone resins.

As the anode, an electrode made of a material such as a metal, an alloy, a conductive compound and a mixture of these materials which has a great work function (4 eV or more) is preferably used. Specific examples of the material for the anode include metals such as Au and conductive materials such as CuIn, ITO (indium tin oxide), $SnO_2$, ZnO and In—Zn—O. The anode can be prepared by forming a thin film of the electrode material described above in accordance with a process such as the vapor deposition process and the sputtering process. When the light emitted from the light emitting medium layer is obtained through the anode, it is preferable that the anode has a transmittance of the emitted light greater than 10%. It is also preferable that the sheet resistivity of the anode is several hundred $\Omega/\square$ or smaller. The thickness of the anode is, in general, selected in the range of 10 nm to 1 μm and preferably in the range of 10 to 200 nm although the preferable range may be different depending on the used material.

As the cathode, an electrode made of a material such as a metal, an alloy, a conductive compound and a mixture of these materials which has a small work function (4 eV or smaller) is used. Specific examples of the material for the cathode include sodium, sodium-potassium alloys, magnesium, lithium, magnesium silver mixtures, aluminum/aluminum oxide, $Al/Li_2O$, $Al/LiO_2$, Al/LiF, aluminum lithium alloys, indium and rare earth metals.

The cathode can be prepared by forming a thin film of the material described above in accordance with a process such as the vapor deposition process and the sputtering process.

When the light emitted from the light emitting medium layer is obtained through the cathode, it is preferable that the cathode has a transmittance of the emitted light greater than 10%. It is also preferable that the sheet resistivity of the cathode is several hundred $\Omega/\square$ or smaller. The thickness of the cathode is, in general, selected in the range of 10 nm to 1 μm and preferably in the range of 50 to 200 nm.

In the organic EL device of the present invention, it is preferable that a layer of a chalcogenide, a metal halide or a metal oxide is disposed on the surface of at least one of the pair of electrodes prepared as described above. Specifically, it is preferable that a layer of a chalcogenide (including an oxide) of a metal such as silicon and aluminum is disposed on the surface of the anode at the side of the light emitting medium layer and a layer of a metal halide or a metal oxide is disposed on the surface of the cathode at the side of the light emitting medium layer. Due to the above layers, stability in driving can be improved.

Preferable examples of the chalcogenide include $SiO_x$ ($1 \leq x \leq 2$), $AlO_x$ ($1 \leq x \leq 1.52$), SiON and SiAlON. Preferable examples of the metal halide include CsF, LiF, $MgF_2$, $CaF_2$ and fluorides of rare earth metals. Preferable examples of the metal oxide include $Cs_2O$, $Li_2O$, MgO, SrO, BaO and CaO.

As the light emitting layer in the organic EL of the present invention, a layer having the combination of the following functions is preferably used.

(1) The injecting function: the function of injecting holes from the anode or the hole injecting layer or injecting electrons from the cathode or the electron injecting layer when an electric field is applied.

(2) The transporting function: the function of transporting injected charges (electrons and holes) by the force of the electric field.

(3) The light emitting function: the function of providing the site for recombination of electrons and holes and emitting light generated by the recombination.

The easiness of injection of holes may be different from the easiness of injection of electrons. The ability of transporting holes expressed by the mobility of holes may be different from the ability of transporting electrons expressed by the mobility of electrons. It is preferable that either holes or electrons are transported. The above anthracene derivative represented by any of general formulae (I), (II), (II') and (III) satisfies the above three conditions and the light emitting layer can be formed by using the anthracene derivative as the main component.

As one of the materials constituting the light emitting layer of the organic EL device, a substance forming a recombination site can be used. The substance forming a recombination site is a substance which positively provides a site for recombination of electrons and holes injected from the both electrodes or a substance which provides a site where a recombination energy is transported and light is emitted although the recombination of electrons and holes does not take place. Therefore, when the substance forming a recombination site is used in combination, electrons and holes are recombined at portions more concentrated around the center of the light emitting layer and the luminance of light emission can be increased in comparison with the single use of the anthracene derivative.

From the standpoint of the above phenomenon, it is preferable that a substance having a higher quantum yield of fluorescence is used as the substance forming a recombination site in the light emitting layer of the organic EL device of the present invention. In particular, it is more preferable that the substance has a quantum yield of fluorescence of 0.3 to 1.0. As the substance forming a recombination site, a compound selected from styrylamine compounds, quinacridone derivatives, rubrene derivatives, coumarine derivatives, perylene derivatives, pyrane derivatives and fluoranthene derivatives or a mixture of compounds selected from these compounds is used. Further examples of the substance forming a recombination site include conjugated macromolecular compounds such as polyarylenevinylene derivatives and polyarylene and vinylene derivatives substituted with alkyl groups and alkoxy groups having 1 to 50 carbon atoms.

It is preferable that the substance forming a recombination site is selected in accordance with the color of light emitted from the light emitting layer. For example, when emission of blue light is desired, it is preferable that perylene, a styrylamine derivative or a distyrylarylene derivative substituted with an amino group is used. When emission of green light is desired, it is preferable that a quinacridone derivative or a coumarine derivative is used. When emission of yellow light is desired, it is preferable that a rubrene derivative is used. When emission of orange light or reddish orange light is desired, it is preferable that a dicyanomethylpyrane derivative is used.

In the present invention, it may be preferable that the anthracene derivative represented by any of general formulae (I), (II), (II') and (III) of the present invention is used as the substance forming a recombination site.

In the organic EL device of the present invention, the amount of the substance forming a recombination site used in the device is decided in accordance with the luminance of light emission and the color of emitted light of the light emitting layer. It is preferable that the amount is in the range of 0.1 to 20 parts by mass per 100 parts by mass of the organic compound described above. When the amount of the substance forming a recombination site is less than 0.1 parts by mass, the luminance of light emission tends to decrease. When the amount exceeds 20 parts by mass, heat resistance tends to decrease. Therefore, to maintain an excellent balance between the luminance of the light emission and the heat resistance in the organic EL device, it is preferable that the amount is 0.5 to 20 parts by mass and more preferably 1.0 to 10 parts by mass per 100 parts by mass of the organic compound described above.

As the material constituting the organic light emitting layer of the organic EL device, compounds shown in the following are used in addition to the above compounds in accordance with the desired hue. For example, to obtain light emission in the region of ultraviolet region to purple, a compound represented by the following general formula (IV) is preferably used:

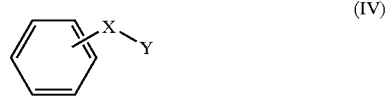
(IV)

wherein X represents a divalent group represented by the following general formula:

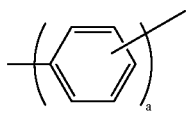

a representing an integer of 2 to 5, and Y represents an aryl group expressed by the following formula:

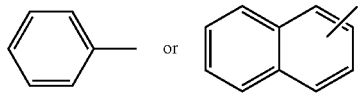

In the compound represented by general formula (IV), phenyl group, phenylene group and naphthyl group may have a single or a plurality of substituents selected from alkyl groups having 1 to 4 carbon atoms, alkoxy groups having 1 to 4 carbon atoms, hydroxyl group, sulfonyl group, carbonyl group, amino group, dimethylamino group and diphenylamino group. When there are a plurality of these groups, the groups may be bonded to each other and form a saturated five-membered or six-membered group. In the compound, it is preferable that the bond is formed at the para-position of phenyl group, phenylene group and naphthyl group since the bonding is rigid and a smooth film is formed by vapor deposition without chemical decomposition. Specific examples of the compound represented by general formula (IV) include the compounds expressed by the following formulae.

In the following formulae, Me represents methyl group, t-Bu represents tertiary-butyl group and Ph represents phenyl group.

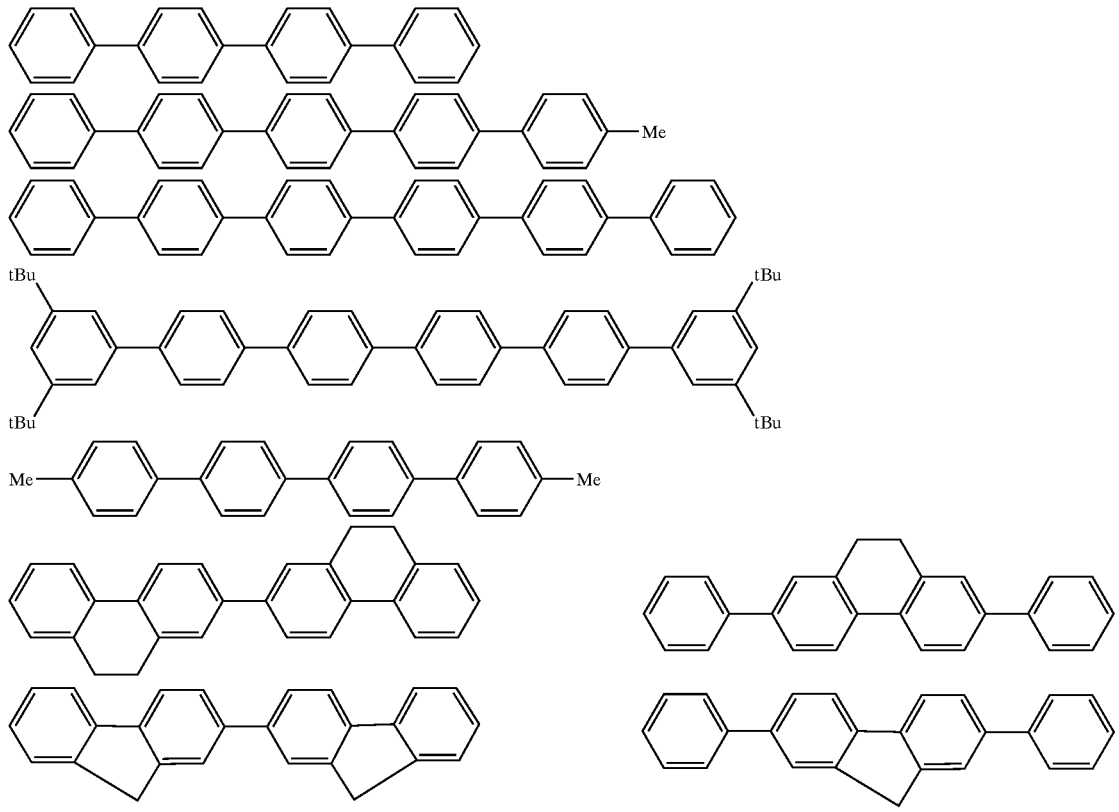

-continued

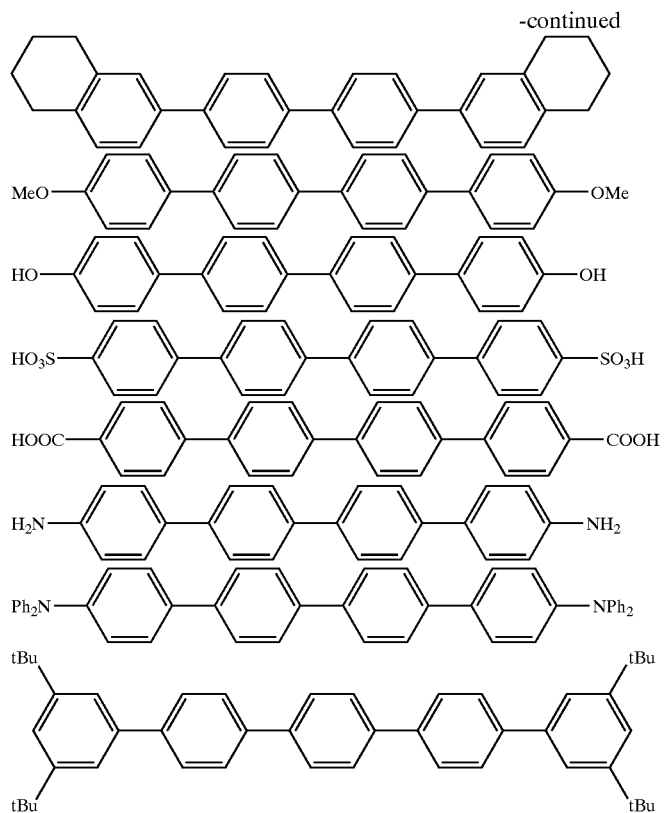

Among the compounds shown in the above, p-quarterphenyl derivatives and p-quinquephenyl derivatives are preferable.

To obtain emission of blue to green light, for example, a fluorescent whitening agent of benzothiazole, benzimidazole or benzoxazole, a metal chelate compound of an oxinoid compound or a styrylbenzene compound can be used. Examples of the above compounds include compounds disclosed in Japanese Patent Application Laid-Open No. Showa 59(1984)-194393. Further examples of the compound useful as the above compounds include compounds listed in Chemistry of Synthetic Dies, 1971, pages 628 to 637 and 640.

As the metal chelate compound of an oxinoid compound, for example, compounds disclosed in Japanese Patent. Application Laid-Open No. Showa 63(1988)-295695 can be used. Typical examples of the above compound include metal complexes of 8-hydroxyquinolines such as tris(8-quinolinol)aluminum and dilithium-epintridione.

As the styrylbenzene compound, for example, compounds disclosed in European Patent Nos. 0319881 and 0373582 can be used. Distyrylpyrazine derivatives disclosed in Japanese Patent Application Laid-Open No. Heisei 2(1990)-252793 can also be used as the material of the light emitting layer. Polyphenyl compounds disclosed in European Patent No. 0387715 can also be used as the material of the light emitting layer.

Compounds other than the fluorescent whitening agents, metal chelate compounds of oxinoid compounds and styrylbenzene compounds can be used as the material of the light emitting layer. Examples of such compounds include the following compounds: 12-phthaloperinone (J. Appl. Phys., Volume 27, L713 (1988)); 1,4-diphenyl-1,3-butadiene and 1,1,4,4-tetraphenyl-1,3-butadiene (Appl. Phys, Lett., Volume 56, L799 (1990)); naphthalimide derivatives (Japanese Patent Application Laid-Open No. Heisei 2(1990)-305886); perylene derivatives (Japanese Patent Application Laid-Open No. Heisei 2 (1990)-189890); oxadiazole derivatives (Japanese Patent Application Laid-Open No. Heisei 2 (1990)-216791 and HAMADA et al., the 38th Associated Meeting of Applied Physics); aldazine derivatives (Japanese Patent Application Laid-Open No. Heisei 2 (1990)-220393); pyrazine derivatives (Japanese Patent Application Laid-Open No. Heisei 2 (1990)-220394); cyclopentadiene derivatives (Japanese Patent Application Laid-Open No. Heisei 2 (1990)-289675); pyrrolopyrrol derivatives (Japanese Patent Application Laid-Open No. Heisei 2 (1990)-296891); styrylamine derivatives (Appl. Phys. Lett., Volume 56, L799 (1990); coumarine compounds (Japanese Patent Application Laid-Open No. Heisei 2 (1990)-191694); and macromolecular compounds described in International Patent Application Publication WO90/13148 and Appl. Phys. Lett., Vol. 158, 18, P1982 (1991).

In the present invention, it is preferable, in particular, that aromatic dimethylidine compounds disclosed in European Patent No. 0388768 and Japanese Patent Application Laid-Open No. Heisei 3 (1991)-231970 are used as the material of the light emitting layer. Examples of the above compounds include 4,4'-bis(2,2-di-t-butylphenylvinyl)biphenyl, 4,4'-bis(2,2-diphenylvinyl)biphenyl and derivatives of these compounds.

Further examples of the compounds which are used as the material of the light emitting layer include compounds represented by the general formula $(Rs-Q)_2$—Al—O—L which are described in Japanese Patent Application Laid-Open No. Heisei 5(1993)-258862. In the general formula, L represents a hydrocarbon group having 6 to 24 carbon atoms which comprises a phenyl portion, O—L represents a phenolate ligand, Q represents a 8-quilinolate ligand and Rs represents a substituent to the 8-quinolinolate ring which is selected so as to inhibit coordination of more than two 8-quinolinolate ligands to the aluminum atom. Specific examples of the above compound include bis(2-methyl-8-quinolinolato)(para-phenylphenolato)aluminum(III) and bis (2-methyl-8-quinolinolato)(1-naphtholato)aluminum(III).

Mixed emission of blue light and green light can be obtained in a high efficiency in accordance with the doping method as disclosed in Japanese Patent Application Laid-Open No. Heisei 6 (1994)-9953. In this method, the light emitting material described above can be used as the host. As the dopant, a fluorescent die having strong blue to green color such as a coumarine fluorescent die and the same fluorescent die as that used for the host can be used. Specifically, a light emitting material having a distyrylarylene skeleton structure and preferably 4,4'-bis(2,2-diphenylvinyl)biphenyl is used as the host and a perylene derivative and preferably, for example, a distyrylarylene derivative is used as the dopant.

The light emitting layer for obtaining emission of white light is not particularly limited. The following light emitting layers may be used:

(1) A light emitting layer in which the energy level of each layer in an organic EL laminate is specified and light is emitted utilizing the tunnel injection (European Patent No. 0390551).

(2) A light emitting device emitting white light which is described in an example of a device utilizing the tunnel injection similarly to the device in (1) (Japanese Patent Application Laid-Open No. Heisei 3(1991)-230584).

(3) A light emitting layer having a two-layer structure (Japanese Patent Application Laid-Open Nos. Heisei 2(1990)-220390 and Heisei 2(1990)-216790).

(4) A light emitting layer divided into a plurality of layers each of which is composed of a material having a different wavelength of emitted light (Japanese Patent Application Laid-Open No. Heisei 4(1992)-51491).

(5) A light emitting layer in which a light emitting material emitting blue light (the peak wavelength of the fluorescence: 380 to 480 nm) and a light emitting material emitting green light (the peak wavelength of the fluorescence: 480 to 580 nm) are laminated and a fluorescent material emitting red light is further contained (Japanese Patent Application Laid-Open No. Heisei 6(1994)-207170).

(6) A light emitting layer in which a light emitting layer emitting blue light contains a fluorescent die emitting blue light, a light emitting layer emitting green light has an area containing a fluorescent die emitting red light and a fluorescent material emitting green light is further contained (Japanese Patent Application Laid-Open No. Heisei 7(1995)-142169).

Among these light emitting layers, the light emitting layer having structure (5) is preferably used.

As the fluorescent material emitting red light, compounds shown in the following are preferably used.

In the following formulae, Me represents methyl group, iPr represents isopropyl group and Et represents ethyl group.

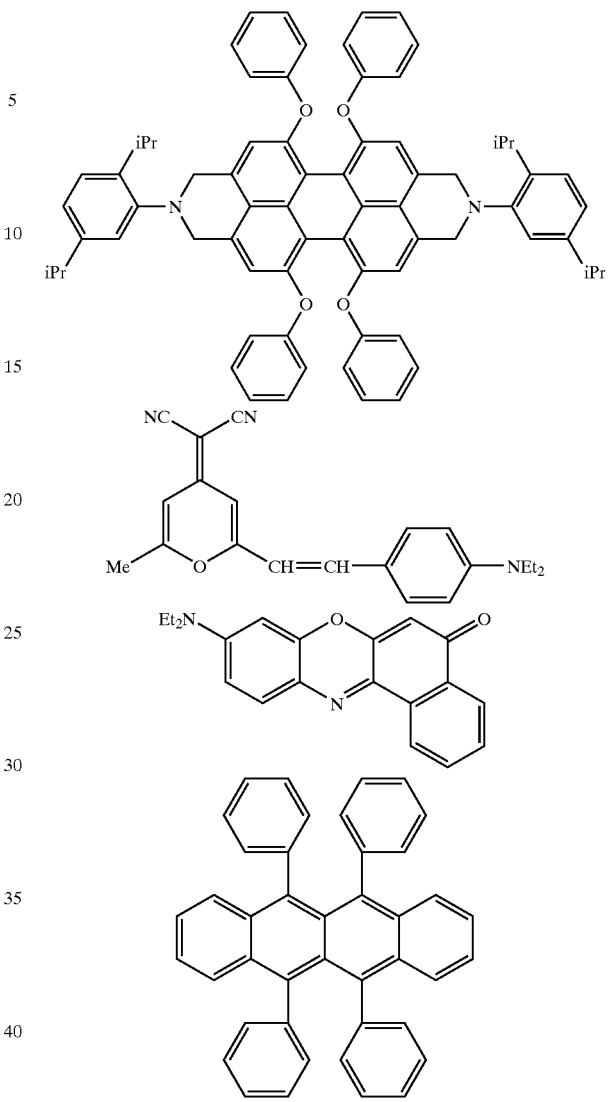

As the process for forming the light emitting layer using the above materials, for example, a conventional process such as the vapor deposition process, the spin coating process and the Langmuir-Blodgett process (the LB process) can be used. In particular, it is preferable that the light emitting layer is a molecular deposition film. The molecular deposition film is a film formed by deposition of a material compound in the gas phase or a film formed by solidification of a material compound in a solution or in the liquid state. The molecular deposition film can be distinguished from a thin film formed by the LB process (a molecular accumulation film) based on differences in the aggregation structure and the higher order structures and functional differences due to these structural differences.

As disclosed in Japanese Patent Application Laid-Open No. Showa 57(1982)-51781, the light emitting layer can also be formed by dissolving a binding material such as a resin and a material compound into a solvent to prepare a solution, followed by forming a thin film in accordance with the spin coating process.

The thickness of the light emitting layer thus formed is not particularly limited and can be suitably selected in accordance with the situation. It is preferable that the thickness is in the range of 5 nm to 5 μm. The light emitting layer may be constituted with a single layer comprising one or more materials selected from the above materials or may be a laminate of the above light emitting layer with a light emitting layer comprising a compound different from the compound comprised in the above light emitting layer.

The hole injecting and transporting layer is a layer which helps injection of holes into the light emitting layer and transports holes to the light emitting area. This layer has a great mobility of holes and the ionization energy is, in general, as small as 5.5 eV or smaller. For the hole injecting and transporting layer, a material transporting holes to the light emitting layer under a small electric field strength is preferable. It is preferable that the mobility of holes is, for example, at least $10^{-6}$ cm$^2$/V.sec when an electric field of $10^4$ to $10^6$ V/cm is applied. The material which is mixed with the distyrylarylene derivative of the present invention and forms the hole injecting and transporting layer is not particularly limited as long as the material has the desirable properties described above. A material can be suitably selected from materials conventionally used as the hole transporting material in optically conductive materials and materials conventionally used for a hole injecting layer in EL devices.

Examples of the material forming the hole injecting and transporting layer are as follows: triazole derivatives (U.S. Pat. No. 3,112,197); oxadiazole derivatives (U.S. Pat. No. 3,189,447); imidazole derivatives (Japanese Patent Application Publication No. Showa 37(1962)-16096); polyarylalkane derivatives (U.S. Pat. Nos. 3,615,402, 3,820,989 and 3,542,544, Japanese Patent Application Publication Nos. Showa 45(1970)-555 and Showa 51(1976)-10983 and Japanese Patent Application Laid-Open Nos. Showa 51(1976)-93224, Showa 55(1980)-17105, Showa 56(1981)-4148, Showa 55(1980)-108667, Showa 55(1980)-156953 and Showa 56(1981)-36656); pyrazoline derivatives and pyrazolone derivatives (U.S. Pat. Nos. 3,180,729 and 4,278,746 and Japanese Patent Application Laid-Open Nos. Showa 55(1980)-88064, Showa 55(1980)-88065, Showa 49(1974)-105537, Showa 55(1980)-51086, Showa 56(1981)-80051, Showa 56(1981)-88141, Showa 57(1982)-45545, Showa 54(1979)-112637 and Showa 55(1980)-74546); phenylenediamine derivatives (U.S. Pat. No. 3,615,404, Japanese Patent Application Publication Nos. Showa 51(1976)-10105, Showa 46(1971)-3712 and Showa 47(1972)-25336 and Japanese Patent Application Laid-Open Nos. Showa 54(1979)-53435, Showa 54(1979)-110536 and Showa 54(1979)-119925); arylamine derivatives (U.S. Pat. Nos. 3,567,450, 3,180,703, 3,240,597, 3,658,520, 4,232,103, 4,175,961 and 4,012,376, Japanese Patent Application Publication Nos. Showa 49(1974)-35702 and Showa 39(1964)-27577, Japanese Patent Application Laid-Open Nos. Showa 55(1980)-144250, Showa 56(1981)-119132 and Showa 56(1981)-22437 and West German Patent No. 1,110,518); chalcone derivatives substituted with amines (U.S. Pat. No. 3,526,501); oxazole derivatives (U.S. Pat. No. 3,257,203); styrylanthracene derivatives (Japanese Patent Application Laid-Open No. Showa 56(1981)-46234); fluorenone derivatives (Japanese Patent Application Laid-Open No. Showa 54(1979)-110837); hydrazone derivatives (U.S. Pat. No. 3,717,462 and Japanese Patent Application Laid-Open Nos. Showa 54(1979)-59143, Showa 55(1980)-52063, Showa 55(1980)-52064, Showa 55(1980)-46760, Showa 55(1980)-85495, Showa 57(1982)-11350, Showa 57(1982)-148749 and Heisei 2(1990)-311591); stilbene derivatives (Japanese Patent Application Laid-Open Nos. Showa 61(1986)-210363, Showa 61(1986)-228451, Showa 61(1986)-14642, Showa 61(1986)-72255, Showa 62(1987)-47646, Showa 62(1987)-36674, Showa 62(1987)-10652, Showa 62(1987)-30255, Showa 60(1985)-93455, Showa 60(1985)-94462, Showa 60(1985)-174749 and Showa 60(1985)-175052); Silazane derivatives (U.S. Pat. No. 4,950,950); polysilane compounds (Japanese Patent Application Laid-Open No. Heisei 2(1990)-204996); aniline copolymers (Japanese Patent Application Laid-Open No. Heisei 2(1990)-282263); and electrically conductive macromolecular oligomers, in particular, thiophene oligomers (Japanese Patent Application Laid-Open No. Heisei 1(1989)-211399).

As the material of the hole injecting layer, the above materials can be used. The following materials can also be used as the material of the hole injecting layer: porphyrin compounds (Japanese Patent Application Laid-Open No. Showa 63(1988)-295695); aromatic tertiary-amine compounds and styrylamine compounds (U.S. Pat. No. 4,127,412 and Japanese Patent Application Laid-Open Nos. Showa 53(1978)-27033, Showa 54(1979)-58445, Showa 54(1979)-149634, Showa 54(1979)-64299, Showa 55(1980)-79450, Showa 55(1980)-144250, Showa 56(1981)-119132, Showa 61(1986)-295558, Showa 61(1986)-98353 and Showa 63(1988)-295695).

Further examples include compounds having two condensed aromatic rings in the molecule which are disclosed in U.S. Pat. No. 5,061,569, such as 4,4'-bis(N-(1-naphthyl)-N-phenylamino)biphenyl and compounds having three triphenylamine units bonded in the star burst form, which are disclosed in Japanese Patent Application Laid-Open No. Heisei 4(1992)-308688, such as 4,4',4"-tris(N-(3-methylphenyl)-N-phenylamino)triphenylamine. Aromatic dimethylidine compounds described above as the material of the light emitting layer and inorganic compounds such as the p-type Si and the p-type SiC can also be used as the material of the hole injecting layer.

To form the hole injecting and transporting layer, a thin film of the above compound is formed in accordance with a conventional process such as the vacuum vapor deposition process, the spin coating process, the casting process and the LB process. The thickness of the hole injecting and transporting layer is not particularly limited. The thickness is, in general, 5 nm to 5 µm. As long as the compound of the present invention is contained in the hole transporting area, the hole injecting and transporting layer may be composed of a single layer comprising one or more materials selected from the materials described above or may be a laminate of the above hole injecting and transporting layer with a hole injecting and transporting layer comprising a compounds different from the compound comprised in the above hole injecting and transporting layer.

The layer of an organic semiconductor is a layer for helping injection of holes or electrons into the light emitting layer. It is preferable that this layer has an electric conductivity of $10^{-10}$ S/cm or greater. As the material of the layer of an organic semiconductor, electrically conductive oligomers such as oligomers containing thiophene, oligomers containing arylamines disclosed in Japanese Patent Application Laid-Open No. Heisei 8(1996)-193191 and electrically conductive dendrimers such as dendrimers containing arylamines can be used.

The electron injecting layer is a layer for helping injection of electrons into the light emitting layer and has a great mobility of electrons. The layer for improving adhesion is the electron injecting layer made of a material exhibiting excellent adhesion with the cathode. As the material used for the electron injecting layer, metal complexes of 8-hydroxyquinoline and derivatives thereof are preferably used. Examples of the metal complexes of 8-hydroxyquinoline and derivatives thereof which can be used as the material for electron injecting layer include metal chelate compounds of oxinoid compounds including chelate compounds of oxine (in general, 8-quinolinol or 8-hydroxyquinoline) such as tris(8-quinolinol)aluminum.

Examples of the oxadiazole derivative include electron transferring compounds represented by the following general formulae (V) to (VII):

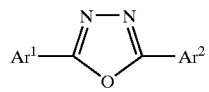
(V)

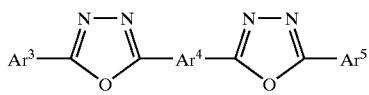
(VI)

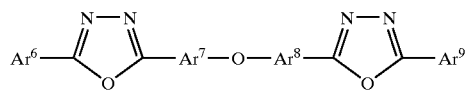
(VII)

wherein $Ar^1$, $Ar^2$, $Ar^3$, $Ar^5$, $Ar^6$ and $Ar^9$ each represent an aryl group which may have substituents, $Ar^1$ and $Ar^2$, $Ar^3$ and $Ar^5$, and $Ar^6$ and $Ar^9$ may represent the same group or different groups, $Ar^4$, $Ar^7$ and $Ar^8$ each represent an arylene group which may have substituents and $Ar^7$ and $Ar^8$ may represent the same group or different groups.

Examples of the aryl group in the above general formulae (V) to (VII) include phenyl group, biphenyl group, anthranyl group, perylenyl group and pyrenyl group. Examples of the arylene group include phenylene group, naphthylene group, biphenylene group, anthranylene group, perylenylene group and pyrenylene group. Examples of the substituent to the above groups include alkyl groups having 1 to 10 carbon atoms, alkoxy groups having 1 to 10 carbon atoms and cyano group. As the electron transferring compound, compounds having the excellent property to form a thin layer are used.

Specific examples of the electron transferring compound include the compounds expressed by the following formulae. In the formulae, Me represents methyl group and t-Bu represents tertiary-butyl group.

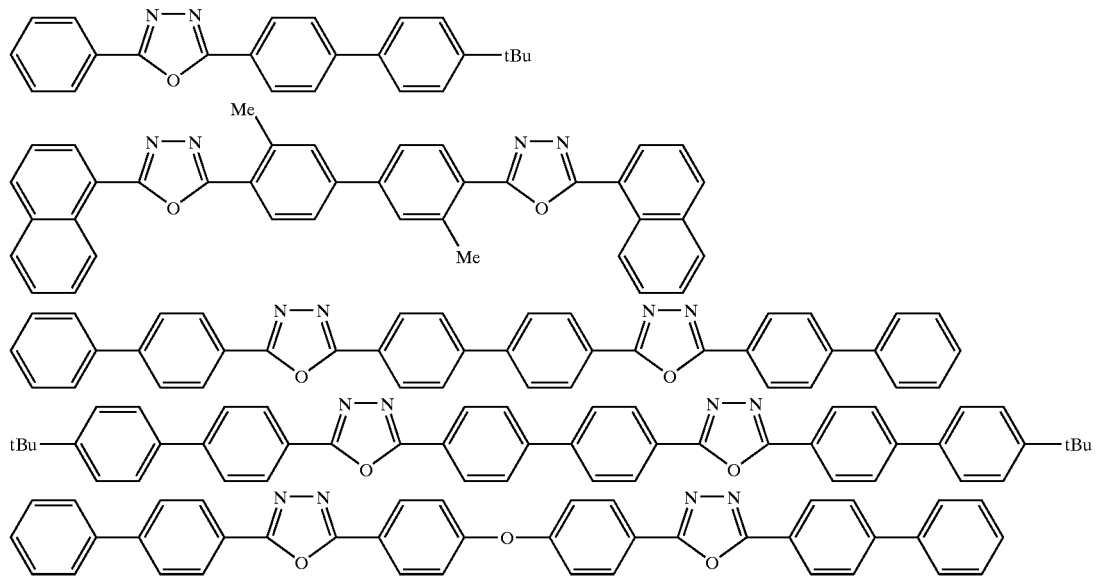

As for the process for preparing the organic EL device of the present invention, the organic EL device can be prepared by forming the anode, the light emitting layer and, where necessary, the hole injecting layer and the electron injecting layer using the above materials in accordance with the above process, followed by forming the cathode. The organic EL device may be prepared in the reverse order, i.e., by preparing the cathode first and the anode last.

As an embodiment, preparation of an organic EL device having the construction in which an anode, a hole injecting layer, a light emitting layer, an electron injecting layer and a cathode are formed on a substrate transmitting light in this order will be described in the following.

The anode is formed first. A thin film of an anode material is formed on the substrate transmitting light in accordance with a process such as the vapor deposition process or the sputtering process so that the formed thin film has a thickness of 1 μm or smaller and preferably in the range of 10 to 200 nm. The hole injecting layer is then formed on the anode. As described above, the hole injecting layer may be formed in accordance with a process such as the vacuum vapor deposition process, the spin coating process, the casting process and the LB process. The vacuum vapor deposition process is preferable since a uniform film can be obtained and the formation of pin holes can be suppressed. When the hole injecting layer is formed in accordance with the vacuum vapor deposition process, the conditions of the vacuum vapor deposition process are different depending on the compound used (the material of the hole injecting layer) and the crystal structure and the recombination structure of the hole injecting layer to be formed. In general, it is preferable that the temperature of the source of the vapor deposition is selected in the range of 50 to 450° C., the degree of vacuum is selected in the range of $10^{-7}$ to $10^{-3}$ torr, the rate of vapor deposition is selected in the range of 0.01 to 50 nm/second, the temperature of the substrate plate is selected in the range of −50 to 300° C. and the thickness of the film is selected in the range of 5 nm to 5 µm.

The light emitting layer is formed on the hole injecting layer. Using a desired organic light emitting material, a thin film of the organic light emitting material is formed in accordance with a process such as the vacuum vapor deposition process, the sputtering process, the spin coating process and the casting process. The vacuum vapor deposition process is preferable since a uniform film can be obtained and the formation of pin holes can be suppressed. When the light emitting layer is formed in accordance with the vacuum vapor deposition process, the conditions of the vacuum vapor deposition process is different depending on the compound used. In general, the conditions can be selected in the same ranges as those described above in the formation of the hole injecting layer.

The electron injecting layer is formed on the light emitting layer formed above. Similarly to the formation of the hole injecting layer and the light emitting layer, it is preferable that the vacuum vapor deposition process is used since the formation of a uniform film is necessary. The conditions of the vacuum vapor deposition process can be selected in the same ranges as those described in the formation of the hole injecting layer and the light emitting layer.

The process for adding the anthracene derivative of the present invention is different depending on the layer in which the anthracene derivative is comprised. When the vacuum deposition process is used, the anthracene derivative can be vacuum vapor deposited simultaneously with other materials. When the spin coating process is used, the anthracene derivative can be used as a mixture with other materials.

The cathode is laminated in the final step and the organic EL device can be obtained. The cathode is constituted with a metal and the vacuum vapor deposition process or the sputtering process can be used for the formation. The vacuum vapor deposition process is preferable since formation of damages in the organic layers formed in previous steps during the formation of the cathode can be prevented.

It is preferable that the steps for preparing the organic EL device from the formation of the anode to the formation of the cathode are conducted after the pressure in the apparatus for the preparation is reduced and while the pressure is maintained at the reduced pressure.

When the organic EL device is used, the light emission can be observed when the anode is connected to the positive electrode (+) and the cathode is connected to the negative electrode (−) and a voltage of 3 to 40 V is applied. When the anode is connected to the negative electrode (−) and the cathode is connected to the positive electrode (+), the light emission is not observed at all. When an alternating voltage is applied, a uniform emission of light is observed only when the anode is connected to the positive electrode (+) and the cathode is connected to the negative electrode (−). The wave form of the applied alternating voltage is not limited.

The present invention will be described more specifically with reference to examples in the following. However, the present invention is not limited to the examples.

EXAMPLE 1

Synthesis of Compound E1

Under the atmosphere of argon, 9.3 g (30 mmol) of 3,5-diphenylbromobenzene was dissolved into a mixed solvent prepared from 50 ml of anhydrous toluene and 50 ml of anhydrous tetrahydrofuran (THF) and the resultant solution was cooled at −20° C. in a methanol bath cooled with dry ice. To the cooled solution, n-butyllithium (1.50 M in hexane; 21 ml; 32 mmol) was added and the resultant mixture was stirred at −20° C. for 1 hour. Then, 3.8 g (10 mmol) of bianthrone was added and the resultant mixture was stirred at −20° C. for 1 hour and at room temperature for 6 hours, successively, and left standing for one night. The reaction mixture was quenched with 50 ml of a saturated aqueous solution of ammonium chloride. The formed solid substance was separated by filtration and washed with water, methanol and acetone and 7.3 g (the yield: 87%) of a diol compound was obtained as a white solid.

Under the atmosphere of argon, 7.3 g (8.6 mmol) of the diol compound obtained above was suspended in 100 ml of acetic acid. To the obtained suspension, a 57% hydroiodic acid (11 ml; 83 mmol; 10 eq) was added and the resultant mixture was stirred at 80° C. for 8 hours. The reaction product was quenched by adding 50 ml of a 50% phosphorous acid. The formed solid substance was separated by filtration and washed with water, methanol and acetone and 5.9 g (the yield: 84%) of a white solid was obtained. The results of measurements with the obtained product in accordance with the elemental analysis and the field desorption mass spectroscopy (FD-MS) were as follows:

Elemental analysis (%): C: 94.52; H: 5.38 (the calculated value (%) as $C_{64}H_{42}$: C: 94.78; H: 5.22)

FD-MS: m/z=810 ($M^+$, 100) (the molecular weight calculated as $C_{64}H_{42}$=810)

EXAMPLE 2

Synthesis of Compound E7

Under the atmosphere of argon, 20 g (64 mmol) of 1,3,5-tribromobenzene and 3.6 g (5.1 mmol; 4% Pd) of dichlorobis-(triphenylphosphine)palladium were dissolved into 500 ml of anhydrous THF. To the resultant solution, a Grignard reagent prepared from 27 g (0.13 mol) of 3-bromoquinoline and 3.7 g (0.16 mol) of magnesium was added dropwise and the resultant mixture was heated under the refluxing condition for 4 hours. The reaction product was quenched by adding water. The organic layer was separated, washed with a saturated aqueous solution of sodium chloride and dried with anhydrous magnesium sulfate. After the solvent was removed by distillation, the product was purified in accordance with the column chromatography (silica gel/hexane+10% dichloromethane) and 8.4 g (the yield: 32%) of a white solid was obtained.

Under the atmosphere of argon, 8.4 g (20 mmol) of the white solid obtained above was dissolved into a mixed solvent prepared from 50 ml of anhydrous toluene and 50 ml of anhydrous THF and the resultant solution was cooled at −20° C. in a methanol bath cooled with dry ice. To the cooled solution, n-butyllithium (1.50 M in hexane; 15 ml; 22 mmol) was added and the resultant mixture was stirred at −20° C. for 1 hour. Then, 2.6 g (6.8 mmol) of bianthrone was added and the resultant mixture was stirred at −20° C. for 1 hour and at room temperature for 6 hours, successively, and left standing for one night. The obtained reaction product was quenched by adding 50 ml of a saturated aqueous solution of ammonium chloride. The formed solid substance was separated by filtration and washed with water, methanol and acetone and 4.8 g (the yield: 67%) of a diol compound was obtained as a white solid. Then, under the atmosphere of argon, 4.8 g (4.6 mmol) of the diol compound obtained above was suspended in 50 ml of acetic acid. To the obtained suspension, a 57% hydroiodic acid (6 ml; 46 mmol; 10 eq) was added and the resultant mixture was stirred at 80° C. for 8 hours. The reaction product was quenched by adding 30 ml of a 50% hypophosphorous acid. The formed solid substance was separated by filtration and washed with water, methanol and acetone and 3.8 g (the yield: 81%) of a white solid was obtained. The results of measurements with the obtained product in accordance with the elemental analysis and the field desorption mass spectroscopy (FD-MS) were as follows:

Elemental analysis (%): C: 89.02; H: 4.22; N: 5.38 (the calculated value (%) as $C_{76}H_{48}N_4$: C: 89.91, H: 4.57; N: 5.52).

FD-MS: m/z=1016 (M$^+$, 100) (the molecular weight calculated as $C_{76}H_{48}N_4$=1016).

EXAMPLE 3
Synthesis of Compound E14

Under the atmosphere of argon, 15 g (38 mmol) of N-(3,5-dibromophenyl)carbazole and 1.1 g (1.5 mmol; 4% Pd) of dichlorobis-(triphenylphosphine)palladium were dissolved into 500 ml of anhydrous THF. To the resultant solution, a Grignard reagent prepared from 6.0 g (38 mmol) of bromobenzene and 1.1 g (46 mmol) of magnesium was added dropwise and the resultant mixture was heated under the refluxing condition for 4 hours. The reaction product was quenched by adding 100 ml of water. The organic layer was separated, washed with a saturated aqueous solution of sodium chloride and dried with anhydrous magnesium sulfate. After the solvent was removed by distillation, the product was purified in accordance with the column chromatography (silica gel/hexane+10% dichloromethane) and 8.0 g (the yield: 53%) of a white solid was obtained.

Under the atmosphere of argon, 8.0 g (20 mmol) of the white solid obtained above was dissolved into a mixed solvent prepared from 50 ml of anhydrous toluene and 50 ml of anhydrous THF and the resultant solution was cooled at −20° C. in a methanol bath cooled with dry ice. To the cooled solution, n-butyllithium (1.50 M in hexane; 15 ml; 22 mmol) was added and the resultant mixture was stirred at −20° C. for 1 hour. Then, 2.6 g (6.8 mmol) of bianthrone was added and the resultant mixture was stirred at −20° C. for 1 hour and at room temperature for 6 hours, successively, and left standing for one night. The obtained reaction product was quenched by adding 50 ml of a saturated aqueous solution of ammonium chloride. The formed solid substance was separated by filtration and washed with water, methanol and acetone and 4.9 g (the yield: 71%) of a diol compound was obtained as a white solid. Then, under the atmosphere of argon, 4.9 g (4.8 mmol) of the diol compound obtained above was suspended in 50 ml of acetic acid. To the obtained suspension, a 57% hydroiodic acid (6 ml; 48 mmol; 10 eq) was added and the resultant mixture was stirred at 80° C. for 8 hours. The reaction product was quenched by adding, 30 ml of a 50% hypophosphorous acid. The formed solid substance was separated by filtration and washed with water, methanol and acetone and 4.4 g (the yield: 92%) of a white solid was obtained. The results of measurements with the obtained product in accordance with the elemental analysis and the field desorption mass spectroscopy (FD-MS) were as follows:

Elemental analysis (%): C: 91.98; H: 4.52; N: 2.64 (the calculated value (%) as $C_{76}H_{48}N_2$: C: 92.28, H: 4.89; N: 2.83)

FD-MS: m/z=988 (M$^+$, 100) (the molecular weight calculated as $C_{76}H_{48}N_2$=988)

EXAMPLE 4
Synthesis of Compound E31

Under the atmosphere of argon, 20 g (64 mmol) of 1,3,5-tribromobenzene and 3.6 g (5.1 mmol; 4% Pd) of dichlorobis-(triphenylphosphine)palladium were dissolved into 500 ml of anhydrous THF. To the resultant solution, a Grignard reagent prepared from 23 g (0.13 mmol) of 2-bromo-5-methylthiophene and 3.7 g (0.16 mol) of magnesium was added dropwise and the resultant mixture was heated under the refluxing condition for 4 hours. The reaction product was quenched by adding 100 ml of water. The organic layer was separated, washed with a saturated solution of sodium chloride and dried with anhydrous magnesium sulfate. After the solvent was removed by distillation, the product was purified in accordance with the column chromatography (silica gel/hexane+10% dichloromethane) and 7.8 g (the yield: 35%) of a white solid was obtained.

Under the atmosphere of argon, 7.8 g (22 mmol) of the white solid obtained above was dissolved into a mixed solvent prepared from 50 ml of anhydrous toluene and 50 ml of anhydrous THF and the resultant solution was cooled at −20° C. in a methanol bath cooled with dry ice. To the cooled solution, n-butyllithium (1.50 M in hexane; 16 ml; 24 mmol) was added and the resultant mixture was stirred at −20° C. for 1 hour. Then, 2.8 g (7.3 mmol) of bianthrone was added and the resultant mixture was stirred at −20° C. for 1 hour and at room temperature for 6 hours, successively, and left standing for one night. The obtained reaction product was quenched by adding 50 ml of a saturated aqueous solution of ammonium chloride. The formed solid substance was separated by filtration and washed with water, methanol and acetone and 5.1 g (the yield: 76%) of a diol compound was obtained as a white solid. Then, under the atmosphere of argon, 5.1 g (5.5 mmol) of the diol compound obtained above was suspended in 50 ml of acetic acid. To the obtained suspension, a 57% hydroiodic acid (6 ml; 48 mmol; 10 eq) was added and the resultant mixture was stirred at 80° C. for 8 hours. The reaction product was quenched by adding 30 ml of a 50% hypophosphorous acid. The formed solid substance was separated by filtration and washed with water, methanol and acetone and 4.5 g (the yield: 92%) of a white solid was obtained. The results of measurements with the obtained product in accordance with the elemental analysis and the field desorption mass spectroscopy (FD-MS) were as follows:

Elemental analysis (%): C: 80.53; H: 4.49 (the calculated value (%) as $C_{60}H_{42}N_2S_4$: C: 80.86, H: 4.75)

FD-MS: m/z=890 (M$^+$, 100) (the molecular weight calculated as $C_{60}H_{42}N_2S_4$=890)

EXAMPLE 5
Preparation of an Organic EL Device

A glass substrate of a size of 25 mm×75 mm×1.1 mm having a transparent electrode of indium tin oxide (manufactured by GEOMATEC Company) was cleaned in isopropyl alcohol by ultrasonic vibration for 5 minutes and then with ozone for 30 minutes under irradiation by ultraviolet light and attached to a substrate holder of a vacuum vapor deposition apparatus.

On the surface of the substrate at the side having the transparent electrode line, a film of N,N'-bis(N,N'-diphenyl-4-aminophenyl)-N,N-diphenyl-4,4'-diamino-1,1'-biphenyl (referred to as a TPD232 film, hereinafter) having a thickness of 60 nm was formed. The formed TPD232 film worked as the hole injecting layer.

On the formed TPD232 film, a film of 4,4'-bis[N-(1-naphthyl)-N-phenyl]biphenyl (referred to as an NPD film, hereinafter) having a thickness of 20 nm was formed. The formed NPD film worked as the hole transporting film.

On the formed NPD film, a film of compound E1 having a thickness of 40 nm was formed. The formed film worked as the light emitting layer.

On the formed film of compound E1, a film of tris(8-quinolinol)aluminum (referred to as an Alq film, hereinafter) having a thickness of 20 nm was formed. The Alq film worked as the electron injecting film.

On the formed Alq film, Li (manufactured by SAES GETTERS Company) and Alq were binary vacuum vapor deposited and an Alq:Li film was formed as the electron injecting layer (an anode).

On the formed Alq:Li film, metallic aluminum was vacuum vapor deposited and a metallic anode was formed. Thus, an organic EL device was formed.

When a voltage of 6 V was applied to the obtained device, emission of blue light was obtained at a maximum luminance of 43,000 cd/m$^2$ and 3.0 cd/A. The spectrum obtained by the device had a peak wavelength at around 450 nm and excellent purity of color having the chromaticity coordinates of (0.150, 0.131) was obtained.

EXAMPLE 6

Preparation of an Organic EL Device

A device was prepared in accordance with the same procedures as those conducted in Example 5 except that the light emitting layer was prepared by using compound E4 in place of compound E1. Using the prepared device, the properties of light emission were confirmed and the test of heat resistance was conducted. The results are shown in Table 1.

The test of heat resistance was conducted in accordance with the following procedures:

Test of Heat Resistance

The luminance of the prepared device was measured and the obtained value was used as the initial luminance ($I_0$). Then, the device was kept in a vessel thermostatted at 85° C. for 500 hours. Then, the device was taken out of the vessel and left standing until the temperature reached the room temperature. The luminance ($I_{500}$) after being kept for 500 hours under the above condition was measured. The decrease in the luminance (%) was obtained in accordance with the following equation and used for evaluating the heat resistance.

Decrease in the luminance $(\%)=(I_0-I_{500})\times 100/I_0$

EXAMPLE 7

Preparation of an Organic EL Device

A device was prepared in accordance with the same procedures as those conducted in Example 5 except that the light emitting layer was prepared by using compound E7 in place of compound E1. Using the prepared device, the properties of light emission were confirmed and the test of heat resistance was conducted. The results are shown in Table 1.

EXAMPLE 8

Preparation of an Organic EL Device

A device was prepared in accordance with the same procedures as those conducted in Example 5 except that the light emitting layer was prepared by using compound E9 in place of compound E1. Using the prepared device, the properties of light emission were confirmed and the test of heat resistance was conducted. The results are shown in Table 1.

EXAMPLE 9

Preparation of an Organic EL Device

A device was prepared in accordance with the same procedures as those conducted in Example 5 except that the light emitting layer was prepared by using compound E13 in place of compound E1. Using the prepared device, the properties of light emission were confirmed and the test of heat resistance was conducted. The results are shown in Table 1.

EXAMPLE 10

Preparation of an Organic EL Device

A device was prepared in accordance with the same procedures as those conducted in Example 5 except that the light emitting layer was prepared by using compound E14 in place of compound E1. Using the prepared device, the properties of light emission were confirmed and the test of heat resistance was conducted. The results are shown in Table 1.

EXAMPLE 11

Preparation of an Organic EL Device

A device was prepared in accordance with the same procedures as those conducted in Example 5 except that the light emitting layer was prepared by using compound E17 in place of compound E1. Using the prepared device, the properties of light emission were confirmed and the test of heat resistance was conducted. The results are shown in Table 1.

EXAMPLE 12

Preparation of an Organic EL Device

A device was prepared in accordance with the same procedures as those conducted in Example 5 except that the light emitting layer was prepared by using compound E31 in place of compound E1. Using the prepared device, the properties of light emission were confirmed and the test of heat resistance was conducted. The results are shown in Table 1.

COMPARATIVE EXAMPLE 1

Preparation of an Organic EL Device

A device was prepared in accordance with the same procedures as those conducted in Example 5 except that the light emitting layer was prepared by using an anthracene compound H1 expressed by the following formula in place of compound E1. Using the prepared device, the properties of light emission were confirmed and the test of heat resistance was conducted. The results are shown in Table 1.

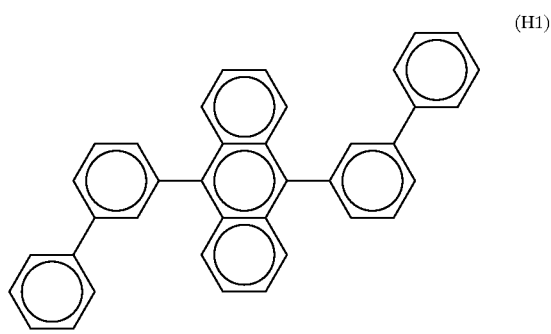

(H1)

EXAMPLE 13

Synthesis of Compound E32

Compound E32 was synthesized in accordance with the following process:

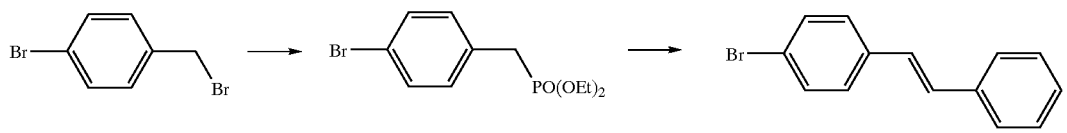

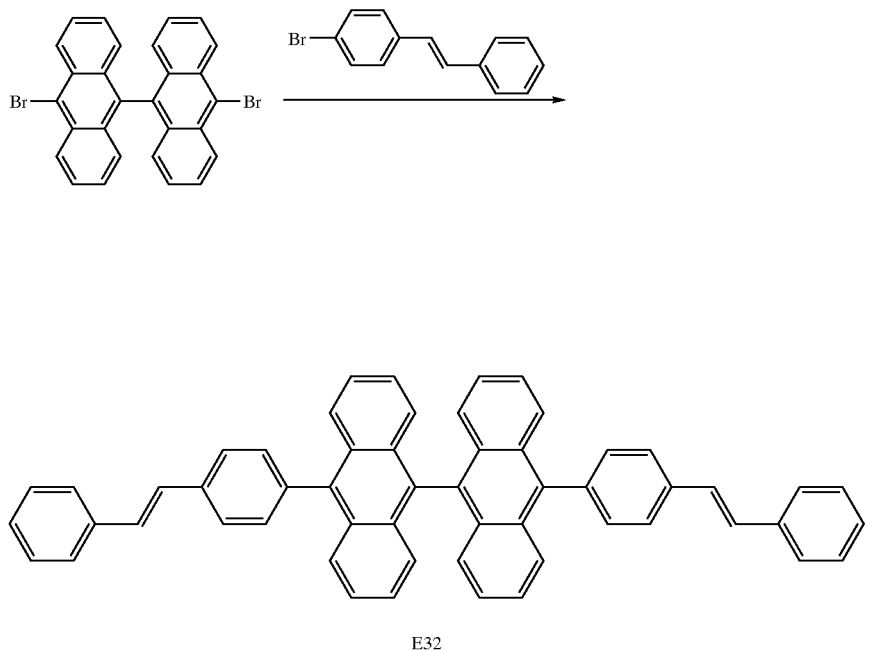

E32

Synthesis of 4-bromostilbene

Into a 100 ml flask, 25 g (0.1 mol) of 4-bromobenzyl bromide and 19 ml (0.11 mol) of triethyl phosphite were placed and the resultant mixture was stirred under heating for 3 hours. After the reaction was completed, the reaction solution was concentrated in vacuo and a phosphite was obtained. The obtained phosphite was used in the following reaction without purification.

In a 500 ml flask, the phosphite obtained above, 10 ml (0.1 mol) of benzaldehyde and 200 ml of dimethyl sulfoxide were placed and cooled at 0° C. with ice water. Then, 13.4 g (0.12 mol) of potassium t-butoxide was slowly added and the resultant mixture was kept being stirred at the room temperature for one night. After the reaction was completed, the reaction solution was poured into 500 ml of water and the organic layer was treated by extraction with ethyl acetate. After drying with magnesium sulfate, the organic layer was concentrated in vacuo using a rotary evaporator and yellow crystals were obtained. The obtained crystals were purified by recrystallization (100 ml of isopropyl alcohol) and 15 g (the yield: 59%) of 4-bromostilbene as the object compound was obtained.

Synthesis of Compound E32

Under a stream of argon, into a 500 ml three-necked flask equipped with a condenser, 1.6 g (66 mmol) of magnesium, a small piece of iodine and 50 ml of THF were placed. After the resultant mixture was stirred at the room temperature for 30 minutes, a solution prepared by dissolving 7.8 g (30 mmol) of 4-bromostilbene into 100 ml of THF was added dropwise. After the addition was completed, the resultant mixture was stirred at 60° C. for 1 hour and a Grignard reagent was prepared.

Under a stream of argon, into a 500 ml three-necked flask equipped with a condenser, 5.1 g (10 mmol) of 10,10'-dibromo-9,9'-bianthryl, 0.4 g (5% by mol) of dichlorobis(triphenylphosphine)palladium, 1 ml (1 M; 1 mmol) of a toluene solution of diisobutylaluminum hydride and 100 ml of THF were placed. To the resultant mixture, the Grignard reagent prepared above was added dropwise at the room temperature. Then, the resultant mixture was heated and stirred under heating for one night. After the reaction was completed, the reaction solution was cooled with ice water. The formed crystals were separated by filtration and washed with 50 ml of methanol and 50 ml of acetone, successively, and 3.5 g of a yellow powder was obtained. The yellow powder was identified to be compound E32 by measurements in accordance with NMR, IR and FD-MS (the yield: 50%).

EXAMPLE 14
Synthesis of Compound E33

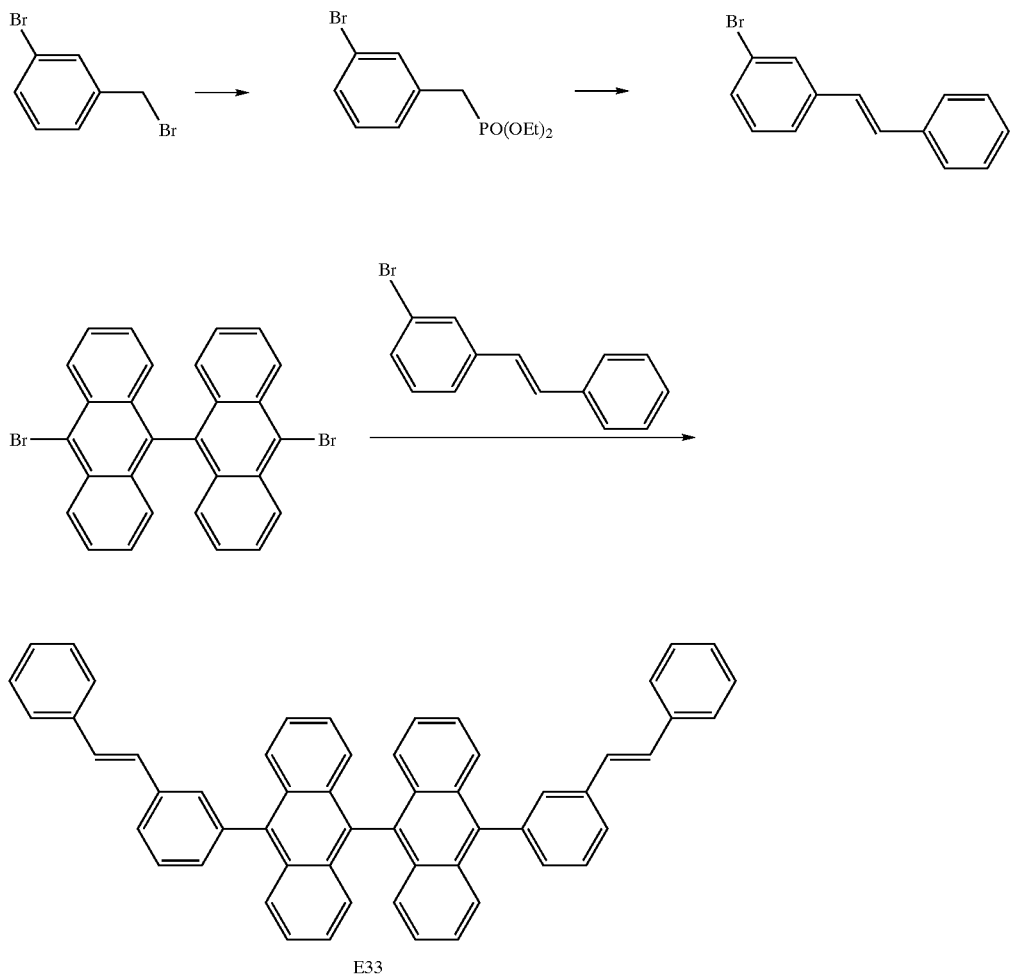

E33

Synthesis of 3-bromostilbene

Into a 100 ml flask, 25 g (0.1 mol) of 3-bromobenzyl bromide and 19 ml (0.11 mol) of triethyl phosphite were placed and the resultant mixture was stirred under heating for 3 hours. After the reaction was completed, the reaction solution was concentrated in vacuo and a phosphite was obtained. The obtained phosphite was used in the following reaction without purification.

In a 500 ml flask, the phosphite obtained above, 10 ml (0.1 mol) of benzaldehyde and 200 ml of dimethyl sulfoxide were placed and cooled at 0° C. with ice water. Then, 13.4 g (0.12 mol) of potassium t-butoxide was slowly added and the resultant mixture was kept being stirred at the room temperature for one night. After the reaction was completed, the reaction solution was poured into 500 ml of water and the organic layer was treated by extraction with ethyl acetate. After drying with magnesium sulfate, the organic layer was concentrated in vacuo using a rotary evaporator and yellow crystals were obtained. The obtained crystals were purified by recrystallization (100 ml of isopropyl alcohol) and 20 g (the yield: 77%) of 3-bromostilbene as the object compound was obtained.

Synthesis of Compound E33

Under a stream of argon, into a 500 ml three-necked flask equipped with a condenser, 1.6 g (66 mmol) of magnesium, Compound E33 was synthesized in accordance with the following process:

a small piece of iodine and 50 ml of THF were placed. After the resultant mixture was stirred at the room temperature for 30 minutes, a solution prepared by dissolving 7.8 g (30 mmol) of 3-bromostilbene into 100 ml of THF was added dropwise. After the addition was completed, the resultant mixture was stirred at 60° C. for 1 hour and a Grignard reagent was prepared.

Under a stream of argon, into a 500 ml three-necked flask equipped with a condenser, 5.1 g (10 mmol) of 10,10'-dibromo-9,9'-bianthryl, 0.4 g (5% by mol) of dichlorobis (triphenylphosphine)palladium, 1 ml (1 M; 1 mmol) of a toluene solution of diisobutylaluminum hydride and 100 ml of THF were placed. To the resultant mixture, the Grignard reagent prepared above was added dropwise at the room temperature. Then, the resultant mixture was heated and stirred under heating for one night. After the reaction was completed, the reaction solution was cooled with ice water. The formed crystals were separated by filtration and washed with 50 ml of methanol and 50 ml of acetone, successively, and 1.4 g of a yellow powder was obtained. The yellow powder was identified to be compound E33 by measurements in accordance with NMR, IR and FD-MS (the yield: 20%).

EXAMPLE 15

Synthesis of Compound 35

Compound E35 was synthesized in accordance with the following process:

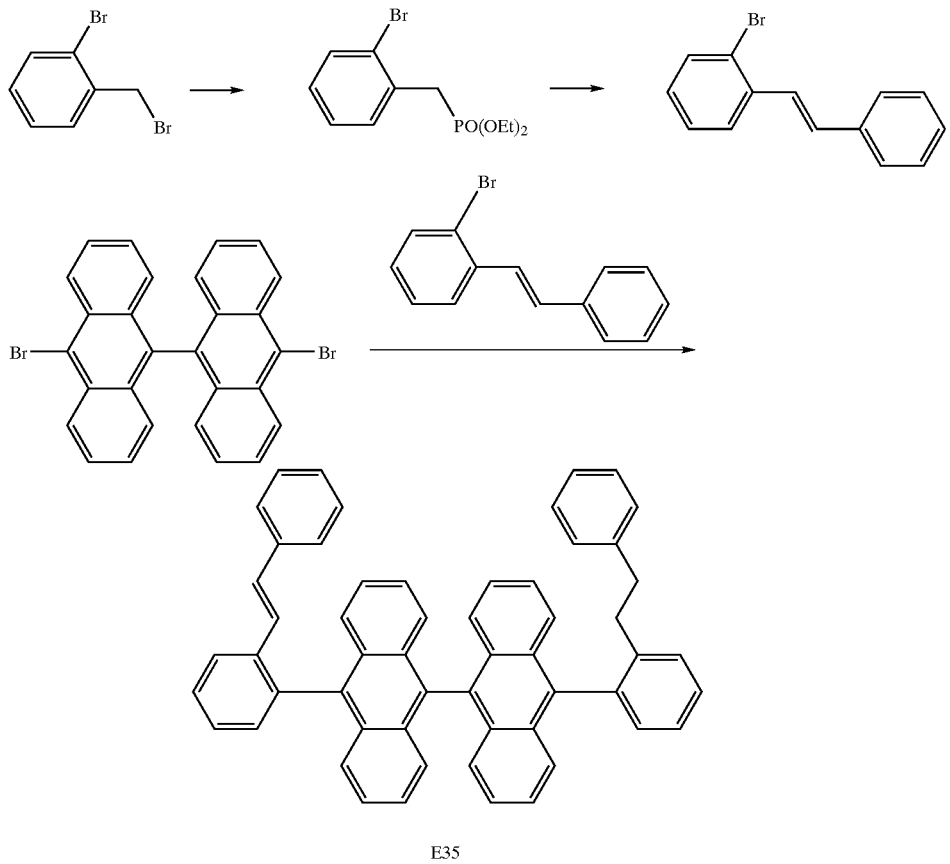

E35

Synthesis of 2-bromostilbene

Into a 100 ml flask, 25 g (0.1 mol) of 2-bromobenzyl bromide and 19 ml (0.11 mol) of triethyl phosphite were placed and the resultant mixture was stirred under heating for 3 hours. After the reaction was completed, the reaction solution was concentrated in vacuo and a phosphite was obtained. The obtained phosphite was used in the following reaction without purification.

In a 500 ml flask, the phosphite obtained above, 10 ml (0.1 mol) of benzaldehyde and 200 ml of dimethyl sulfoxide were placed and cooled at 0° C. with ice water. Then, 13.4 g (0.12 mol) of potassium t-butoxide was slowly added and the resultant mixture was kept being stirred at the room temperature for one night. After the reaction was completed, the reaction solution was poured into 500 ml of water and the organic layer was treated by extraction with ethyl acetate. After drying with magnesium sulfate, the organic layer was concentrated in vacuo using a rotary evaporator and yellow crystals were obtained. The obtained crystals were purified in accordance with the column chromatography (silica gel; the developing solvent: hexane) and 24 g (the yield: 92%) of 2-bromostilbene as the object compound was obtained.

Synthesis of Compound E35

Under a stream of argon, into a 500 ml three-necked flask equipped with a condenser, 1.6 g (66 mmol) of magnesium, a small piece of iodine and 50 ml of THF were placed. After the resultant mixture was stirred at the room temperature for 30 minutes, a solution prepared by dissolving 7.8 g (30 mmol) of 2-bromostilbene into 100 ml of THF was added dropwise. After the addition was completed, the resultant mixture was stirred at 60° C. for 1 hour and a Grignard reagent was prepared.

Under a stream of argon, into a 500 ml three-necked flask equipped with a condenser, 5.1 g (10 mmol) of 10,10'-dibromo-9,9'-bianthryl, 0.4 g (5% by mol) of dichlorobis (triphenylphosphine)palladium, 1 ml (1 M; 1 mmol) of a toluene solution of diisobutylaluminum hydride and 100 ml of THF were placed. To the resultant mixture, the Grignard reagent prepared above was added dropwise at the room temperature. Then, the resultant mixture was heated and stirred under heating for one night. After the reaction was completed, the reaction solution was cooled with ice water. The formed crystals were separated by filtration and washed with 50 ml of methanol and 50 ml of acetone, successively, and 5.7 g of a yellow powder was obtained. The yellow powder was identified to be compound E35 by measurements in accordance with NMR, IR and FD-MS (the yield: 80%).

EXAMPLES 16 to 18

Preparation of an Organic EL Device

Devices were prepared in accordance with the same procedures as those conducted in Example 5 except that the compounds shown in Table 1 were used in place of compound E1. Using the devices prepared in Examples 16 to 18, the properties of light emission were confirmed and the test of heat resistance was conducted. Using the devices prepared in Examples 16 and 17, the chromaticity coordinates were measured. The results are shown in Table 1.

EXAMPLE 19
Synthesis of Compound E42

Compound E42 was synthesized in accordance with the following process:

alcohol) and 12 g (the yield: 44%) of 4-bromo-β-methylstilbene as the object compound was obtained.

Synthesis of Compound E42

Under a stream of argon, into a 500 ml three-necked flask equipped with a condenser, 1.6 g (66 mmol) of magnesium, a small piece of iodine and 50 ml of THF were placed. After the resultant mixture was stirred at the room temperature for

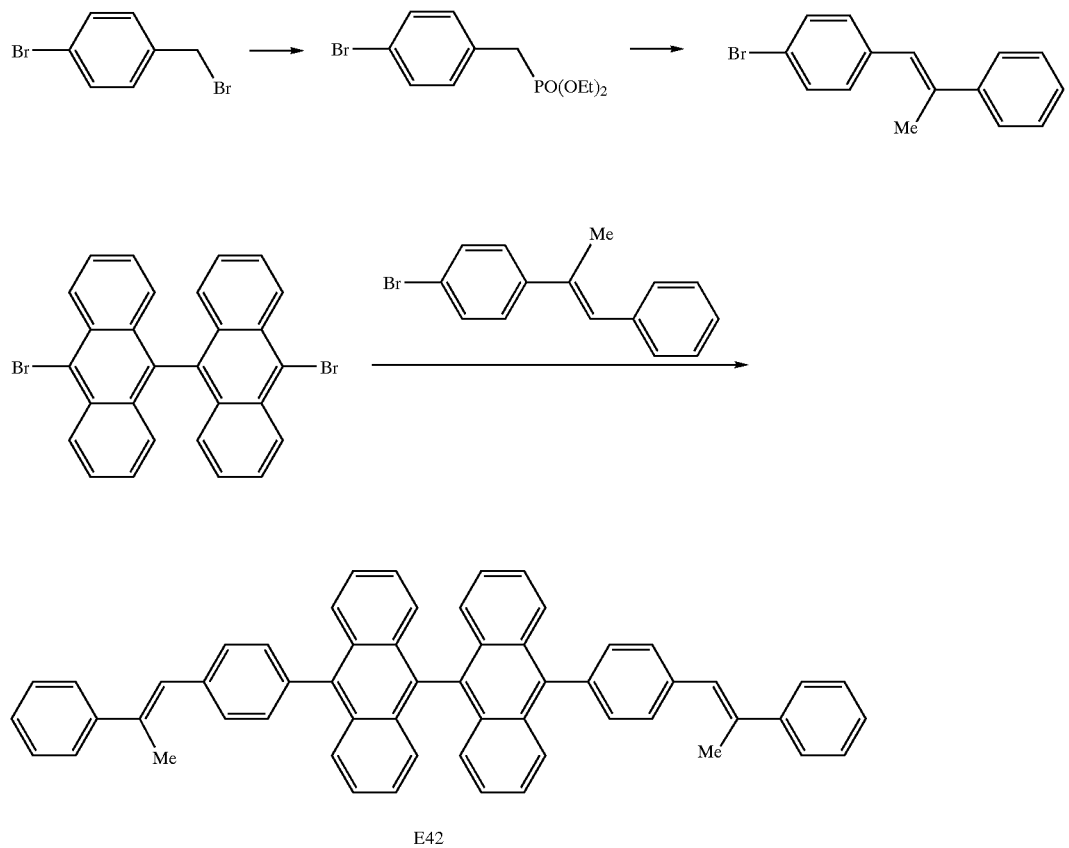

E42

Synthesis of 4-bromo-β-methylstilbene

Into a 100 ml flask, 25 g (0.1 mol) of 4-bromobenzyl bromide and 19 ml (0.11 mol) of triethyl phosphite were placed and the resultant mixture was stirred under heating for 3 hours. After the reaction was completed, the reaction solution was concentrated in vacuo and a phosphite was obtained. The obtained phosphite was used in the following reaction without purification.

In a 500 ml flask, the phosphite obtained above, 12 g (0.1 mol) of acetophenone and 200 ml of dimethyl sulfoxide were placed and cooled at 0° C. with ice water. Then, 13.4 g (0.12 mol) of potassium t-butoxide was slowly added and the resultant mixture was kept being stirred at the room temperature for one night. After the reaction was completed, the reaction solution was poured into 500 ml of water and the organic layer was treated by extraction with ethyl acetate. After drying with magnesium sulfate, the organic layer was concentrated in vacuo using a rotary evaporator and yellow crystals were obtained. The obtained crystals were purified by recrystallization (100 ml of isopropyl 30 minutes, a solution prepared by dissolving 8.2 g (30 mmol) of 4-bromo-β-methylstilbene into 100 ml of THF was added dropwise. After the addition was completed, the resultant mixture was stirred at 60° C. for 1 hour and a Grignard reagent was prepared.

Under a stream of argon, into a 500 ml three-necked flask equipped with a condenser, 5.1 g (10 mmol) of 10,10'-dibromo-9,9'-bianthryl, 0.4 g (5% by mol) of dichlorobis(triphenylphosphine)palladium, 1 ml (1 M; 1 mmol) of a toluene solution of diisobutylaluminum hydride and 100 ml of THF were placed. To the resultant mixture, the Grignard reagent prepared above was added dropwise at the room temperature. Then, the resultant mixture was heated and stirred under heating for one night. After the reaction was completed, the reaction solution was cooled with ice water. The formed crystals were separated by filtration and washed with 50 ml of methanol and 50 ml of acetone, successively, and 4.4 g of a yellow powder was obtained. The yellow powder was identified to be compound E42 by measurements in accordance with NMR, IR and FD-MS (the yield: 60%).

EXAMPLE 20
Synthesis of Compound E43

Compound E43 was synthesized in accordance with the following process:

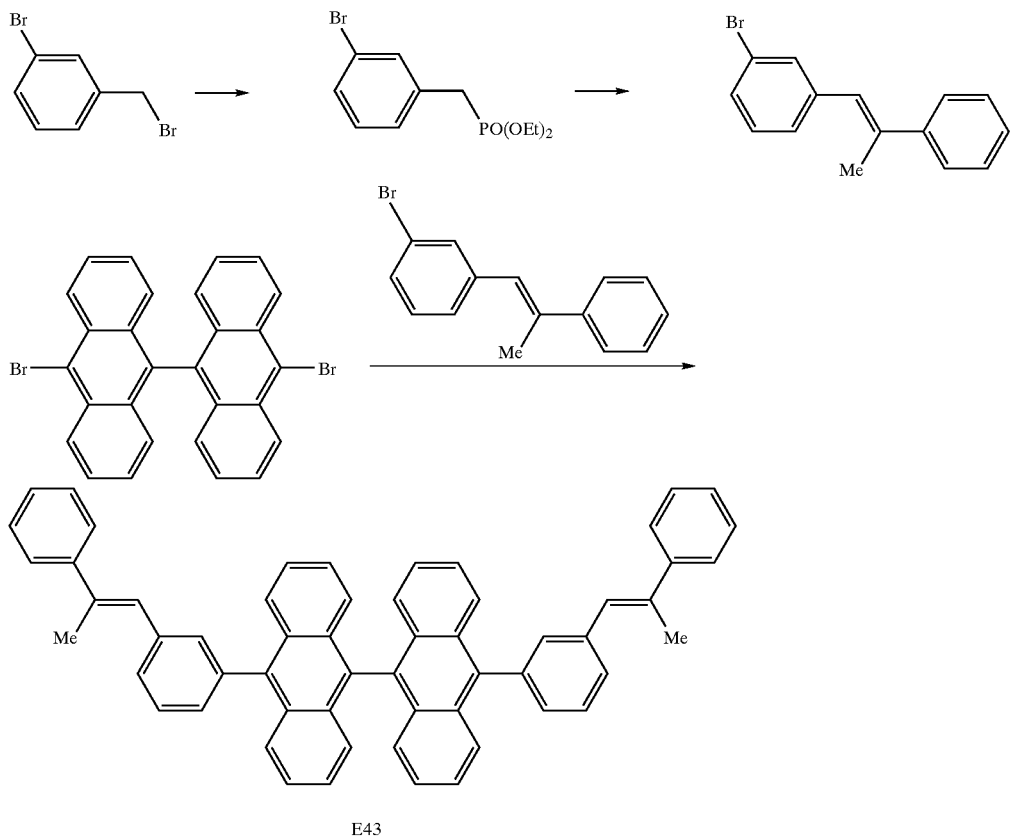

E43

Synthesis of 3-bromo-β-methylstilbene

Into a 100 ml flask, 25 g (0.1 mol) of 3-bromobenzyl bromide and 19 ml (0.11 mol) of triethyl phosphite were placed and the resultant mixture was stirred under heating for 3 hours. After the reaction was completed, the reaction solution was concentrated in vacuo and a phosphite was obtained. The obtained phosphite was used in the following reaction without purification.

In a 500 ml flask, the phosphite obtained above, 12 g (0.1 mol) of acetophenone and 200 ml of dimethyl sulfoxide were placed and cooled at 0° C. with ice water. Then, 13.4 g (0.12 mol) of potassium t-butoxide was slowly added and the resultant mixture was kept being stirred at the room temperature for one night. After the reaction was completed, the reaction solution was poured into 500 ml of water and the organic layer was treated by extraction with ethyl acetate. After drying with magnesium sulfate, the organic layer was concentrated in vacuo using a rotary evaporator and yellow crystals were obtained. The obtained crystals were purified by recrystallization (100 ml of isopropyl alcohol) and 17 g (the yield: 63%) of 3-bromo-β-methylstilbene as the object compound was obtained.

Synthesis of Compound E43

Under a stream of argon, into a 500 ml three-necked flask equipped with a condenser, 1.6 g (66 mmol) of magnesium, a small piece of iodine and 50 ml of THF were placed. After the resultant mixture was stirred at the room temperature for 30 minutes, a solution prepared by dissolving 8.2 g (30 mmol) of 3-bromo-β-methylstilbene into 100 ml of THF was added dropwise. After the addition was completed, the resultant mixture was stirred at 60° C. for 1 hour and a Grignard reagent was prepared.

Under a stream of argon, into a 500 ml three-necked flask equipped with a condenser, 5.1 g (10 mmol) of 10,10'-dibromo-9,9'-bianthryl, 0.4 g (5% by mol) of dichlorobis (triphenylphosphine)palladium, 1 ml (1 M; 1 mmol) of a toluene solution of diisobutylaluminum hydride and 100 ml of THF were placed. To the resultant mixture, the Grignard reagent prepared above was added dropwise at the room temperature. Then, the resultant mixture was heated and stirred under heating for one night. After the reaction was completed, the reaction solution was cooled with ice water. The formed crystals were separated by filtration and washed with 50 ml of methanol and 50 ml of acetone, successively, and 5.3 g of a yellow powder was obtained. The yellow powder was identified to be compound E43 by measurements in accordance with NMR, IR and FD-MS (the yield: 72%).

EXAMPLE 21
Synthesis of Compound E44

Compound E44 was synthesized in accordance with the following process:

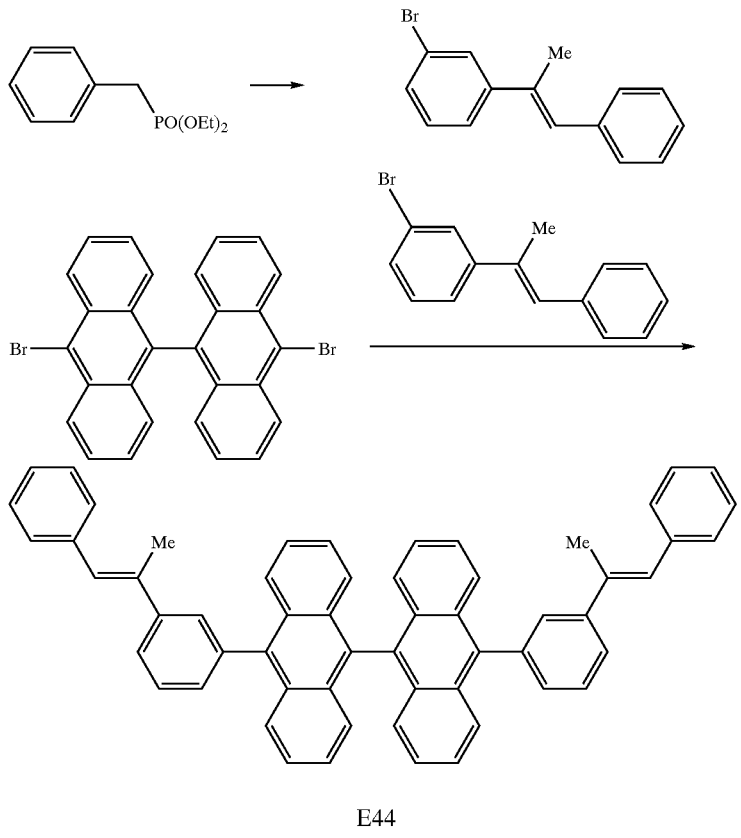

E44

Synthesis of 3-bromo-α-methylstilbene

In a 500 ml flask, 23 g(0.1 mol) of ethyl benzylphosphonate, 20 g (0.1 mol) of 4-bromoacetophenone and 200 ml of dimethyl sulfoxide were placed and cooled at 0° C. with ice water. Then, 13.4 g (0.12 mol) of potassium t-butoxide was slowly added and the resultant mixture was kept being stirred at the room temperature for one night. After the reaction was completed, the reaction solution was poured into 500 ml of water and the organic layer was treated by extraction with ethyl acetate. After drying with magnesium sulfate, the organic layer was concentrated in vacuo using a rotary evaporator. The obtained product were purified in accordance with the column chromatography (silica gel; the developing solvent: hexane) and 26 g (the yield: 88%) of 3-bromo-α-methylstilbene as the object compound was obtained.

Synthesis of Compound E44

Under a stream of argon, into a 500 ml three-necked flask equipped with a condenser, 1.6 g (66 mmol) of magnesium, a small piece of iodine and 50 ml of THF were placed. After the resultant mixture was stirred at the room temperature for 30 minutes, a solution prepared by dissolving 8.2 g (30 mmol) of 3-bromo-a-methylstilbene into 100 ml of THF was added dropwise. After the addition was completed, the resultant mixture was stirred at 60° C. for 1 hour and a Grignard reagent was prepared.

Under a stream of argon, into a 500 ml three-necked flask equipped with a condenser, 5.1 g (10 mmol) of 10,10'-dibromo-9,9'-bianthryl, 0.4 g (5% by mol) of dichlorobis(triphenylphosphine)palladium, 1 ml (1 M; 1 mmol) of a toluene solution of diisobutylaluminum hydride and 100 ml of THF were placed. To the resultant mixture, the Grignard reagent prepared above was added dropwise at the room temperature. Then, the resultant mixture was heated and stirred under heating for one night. After the reaction was completed, the reaction solution was cooled with ice water. The formed crystals were separated by filtration and washed with 50 ml of methanol and 50 ml of acetone, successively, and 5.8 g of a yellow powder was obtained. The yellow powder was identified to be compound E44 by measurements in accordance with NMR, IR and FD-MS (the yield: 79%).

EXAMPLE 22
Measurement of the Glass Transition Temperature

To evaluate the heat resistance, the glass transition temperatures (Tg) of compounds E1, E32, E33 and E42 were measured in accordance with the differential scanning calorimetry (DSC) and found to be 160° C., 163° C., 142° C. and 140° C., respectively. The transition temperatures were all 140° C. or higher.

COMPARATIVE EXAMPLE 2
Measurement of the Glass Transition Temperature

To evaluate the heat resistance, Tg of compound H1 used in Comparative Example 1 was measured in accordance with DSC and found to be as low as 96° C.

EXAMPLE 23
Preparation of an Organic EL Device

A device was prepared in accordance with the same procedures as those conducted in Example 5 except that the light emitting layer was formed by using compound E42 in place of compound E1. Using the prepared device, the properties of light emission were confirmed and the chromaticity coordinates were obtained. The results are shown in Table 1. The maximum luminance of light emission was 30,000 cd/m².

EXAMPLE 24

Preparation of an Organic EL Device

A device was prepared in accordance with the same procedures as those conducted in Example 5 except that the light emitting layer was formed by using compound E43 in place of compound E1. Using the prepared device, the properties of light emission were confirmed and the chromaticity coordinates were obtained. The results are shown in Table 1.

EXAMPLE 25

Preparation of an Organic EL Device

A device was prepared in accordance with the same procedures as those conducted in Example 5 except that the light emitting layer was formed by using compound E44 in place of compound E1. Using the prepared device, the properties of light emission were confirmed and the chromaticity coordinates were obtained. The results are shown in Table 1.

COMPARATIVE EXAMPLE 3

Preparation of an Organic EL Device

A device was prepared in accordance with the same procedures as those conducted in Example 5 except that the light emitting layer was formed by using compound H2 expressed by the following formula in place of compound E1. Using the prepared device, the properties of light emission were confirmed and the chromaticity coordinates were obtained. The results are shown in Table 1.

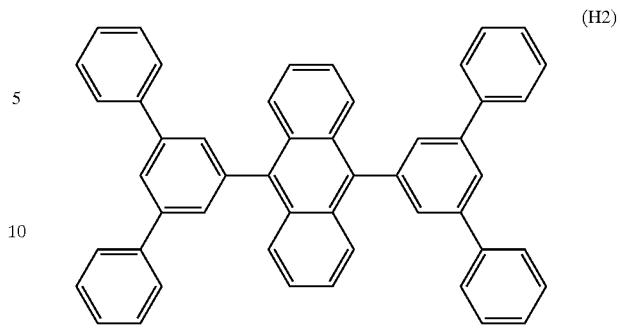

(H2)

COMPARATIVE EXAMPLE 4

Preparation of an Organic EL Device)

A device was prepared in accordance with the same procedures as those conducted in Example 5 except that the light emitting layer was formed by using compound H3 expressed by the following formula in place of compound E1. Using the prepared device, the properties of light emission were confirmed and the chromaticity coordinates were obtained. The results are shown in Table 1.

(H3)

TABLE 1

| | Compound | Voltage (V) | Luminance (nit) | Color of emitted light | Efficiency (cd/A) | Heat resistance (decrease in luminance) (%) | Chromaticity coordinates |
|---|---|---|---|---|---|---|---|
| Example 5 | E1 | 6 | 95 | blue | 3.0 | 5 | (0.150, 0.131) |
| Example 6 | E4 | 6 | 130 | blue | 3.5 | 7 | — |
| Example 7 | E7 | 6 | 161 | blue | 3.7 | 4 | — |
| Example 8 | E9 | 6 | 95 | blue | 2.7 | 3 | — |
| Example 9 | E13 | 6 | 210 | yellowish blue | 7.8 | 12 | — |
| Example 10 | E14 | 6 | 120 | blue | 3.7 | 6 | — |
| Example 11 | E17 | 6 | 60 | bluish green | 4.0 | 5 | — |
| Example 12 | E31 | 6 | 313 | blue | 4.8 | 8 | — |
| Example 16 | E32 | 6 | 210 | blue | 2.2 | 1 | (0.150, 0.135) |
| Example 17 | E33 | 6 | 120 | blue | 4.3 | 2 | (0.171, 0.130) |
| Example 18 | E35 | 6 | 170 | blue | 4.9 | 4 | — |
| Example 23 | E42 | 6 | 157 | bluish purple | 3.0 | — | (0.170, 0.130) |

TABLE 1-continued

|  | Compound | Voltage (V) | Luminance (nit) | Color of emitted light | Efficiency (cd/A) | Heat resistance (decrease in luminance) (%) | Chromaticity coordinates |
|---|---|---|---|---|---|---|---|
| Example 24 | E43 | 6 | 130 | bluish purple | 2.4 | — | (0.155, 0.103) |
| Example 25 | E44 | 6 | 161 | bluish purple | 2.6 | — | (0.155, 0.112) |
| Comparative Example 1 | H1 | 6 | 120 | bluish green | 1.7 | 45 | (0.182, 0.288) |
| Comparative Example 2 | H2 | 6 | 313 | blue | 1.6 | — | (0.162, 0.160) |
| Comparative Example 3 | H3 | 6 | 120 | bluish green | 2.0 | — | (0.210, 0.320) |

As shown in Table 1, the organic EL devices having the light emitting layers formed by using the anthracene derivatives of the present invention exhibited high efficiencies of light emission, small decreases in the luminance and high heat resistances. These properties were exhibited because these anthracene derivatives had high glass transition temperatures of 140° C. or higher and the property of emitting strong fluorescence in the blue to green region. It is also shown that the organic EL devices of the present invention could emit blue light having more excellent purity of color than the light emitted by the devices of the Comparative Examples.

In contrast, the organic EL devices of Comparative Examples 1, 3 and 4 exhibited low efficiencies of light emission. Moreover, the organic EL devices of Comparative Examples 1 and 4 exhibited strongly greenish light and could not be used as a device emitting blue light.

INDUSTRIAL APPLICABILITY

The anthracene derivative of the present invention is useful as the material constituting organic EL devices. In particular, when the anthracene derivative is used as a light emitting material, an excellent efficiency of light emission and excellent heat resistance (life) are exhibited and the obtained device is used as the device having the property of emitting fluorescence in the blue to green region.

What is claimed is:

1. An anthracene derivative represented by formula (I):

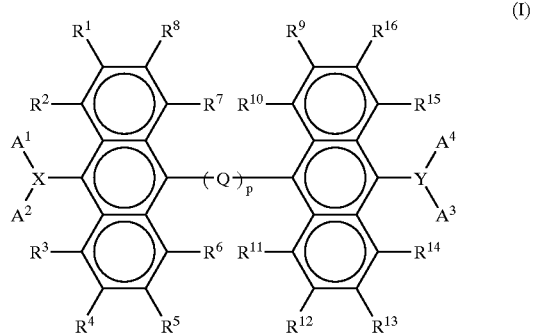

(I)

wherein X and Y each independently represent a substituted or unsubstituted trifunctional aromatic ring group having 6 to 30 carbon atoms or a substituted or unsubstituted trifunctional heterocyclic group having 4 to 30 carbon atoms; $A^1$ to $A^4$ each independently represent a substituted or unsubstituted aryl group having 6 to 30 carbon atoms or a substituted or unsubstituted monovalent heterocyclic group having 4 to 30 carbon atoms; $R^1$ to $R^{16}$ each independently represent hydrogen atom, a halogen atom, cyano group, nitro group, a substituted or unsubstituted alkyl group, a substituted or unsubstituted alkoxy group, a substituted or unsubstituted aryloxy group, a substituted or unsubstituted alkylthio group, a substituted or unsubstituted arylthio group, a substituted or unsubstituted amino group or a substituted or unsubstituted aryl group; adjacent groups represented by $R^1$ to $R^{16}$ may form rings by forming bonds between each other; Q represents a substituted or unsubstituted cycloalkylene group having 5 to 30 carbon atoms, a substituted or unsubstituted arylene group having 6 to 30 carbon atoms or a substituted or unsubstituted divalent heterocyclic group having 4 to 30 carbon atoms; and p represents a number selected from 0, 1 and 2.

2. An anthracene derivative represented by formula (II):

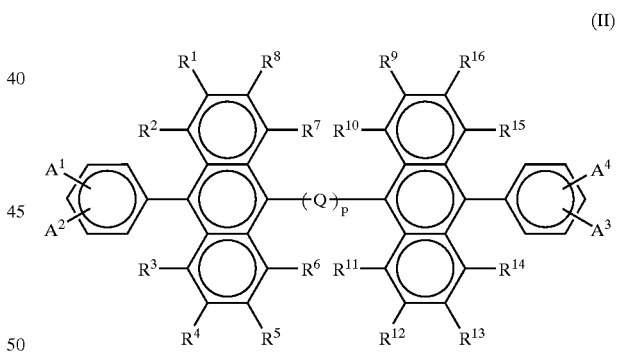

(II)

wherein $A^1$ to $A^4$ each independently represent a substituted or unsubstituted aryl group having 6 to 30 carbon atoms or a substituted or unsubstituted monovalent heterocyclic group having 4 to 30 carbon atoms; $R^1$ to $R^{16}$ each independently represent hydrogen atom, a halogen atom, cyano group, nitro group, a substituted or unsubstituted alkyl group, a substituted or unsubstituted alkoxy group, a substituted or unsubstituted aryloxy group, a substituted or unsubstituted alkylthio group, a substituted or unsubstituted arylthio group, a substituted or unsubstituted amino group or a substituted or unsubstituted aryl group; adjacent groups represented by $R^1$ to $R^{16}$ may form rings by forming bonds between each other; Q represents a substituted or unsubstituted cycloalkylene group having 5 to 30 carbon atoms, a substituted or unsubstituted arylene group having 6 to 30 carbon atoms or a substituted or unsubstituted divalent heterocyclic group having 4 to 30 carbon atoms; and p represents a number selected from 0, 1 and 2.

3. An anthracene derivative represented by formula (II'):

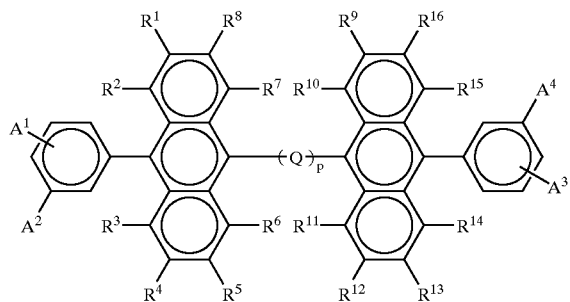

(II')

wherein $A^1$ to $A^4$ each independently represent a substituted or unsubstituted aryl group having 6 to 30 carbon atoms or a substituted or unsubstituted monovalent heterocyclic group having 4 to 30 carbon atoms; $R^1$ to $R^{16}$ each independently represent hydrogen atom, a halogen atom, cyano group, nitro group, a substituted or unsubstituted alkyl group, a substituted or unsubstituted alkoxy group, a substituted or unsubstituted aryloxy group, a substituted or unsubstituted alkylthio group, a substituted or unsubstituted arylthio group, a substituted or unsubstituted amino group or a substituted or unsubstituted aryl group; adjacent groups represented by $R^1$ to $R^{16}$ may form rings by forming bonds between each other; Q represents a substituted or unsubstituted cycloalkylene group having 5 to 30 carbon atoms, a substituted or unsubstituted arylene group having 6 to 30 carbon atoms or a substituted or unsubstituted divalent heterocyclic group having 4 to 30 carbon atoms; and p represents a number selected from 0, 1 and 2.

4. An anthracene derivative represented by general formula (III):

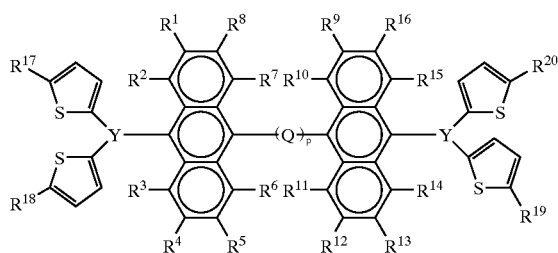

(III)

wherein X and Y each independently represent a substituted or unsubstituted trifunctional aromatic ring group having 6 to 30 carbon atoms or a substituted or unsubstituted trifunctional heterocyclic group having 4 to 30 carbon atoms; $R^1$ to $R^{20}$ each independently represent hydrogen atom, a halogen atom, cyano group, nitro group, a substituted or unsubstituted alkyl group, a substituted or unsubstituted alkoxy group, a substituted or unsubstituted aryloxy group, a substituted or unsubstituted alkylthio group, a substituted or unsubstituted arylthio group, a substituted or unsubstituted amino group or a substituted or unsubstituted aryl group; adjacent groups represented by $R^1$ to $R^{20}$ may for rings by forming bonds between each other; Q represents a substituted or unsubstituted cycloalkylene group having 5 to 30 carbon atoms, a substituted or unsubstituted arylene group having 6 to 30 carbon atoms or a substituted or unsubstituted divalent heterocyclic group having 4 to 30 carbon atoms; and p represents a number selected from 0, 1 and 2.

5. An organic electroluminescence device which comprises a light emitting area comprising an anthracene derivative described in claim 1.

6. An organic electroluminescence device which comprises an organic light emitting layer comprising an anthracene derivative described in claim 1.

7. An organic electroluminescence device according to claim 5, wherein the organic light emitting area further comprises a substance forming a recombination site.

8. An organic electroluminescence device according to claim 6, wherein the organic light emitting layer further comprises a substance forming a recombination site.

9. An organic electroluminescence device according to claim 7, wherein the substance forming a recombination site is a fluorescent substance having a quantum yield of fluorescence of 0.3 to 1.0.

10. An organic electroluminescence device according to claim 8, wherein the substance forming a recombination site is a fluorescent substance having a quantum yield of fluorescence of 0.3 to 1.0.

11. An organic electroluminescence device according to claim 7, wherein the substance forming a recombination site is at least one compound selected from the group consisting of styrylamine compounds, quinacridone derivatives, rubrene derivatives, coumarine derivatives, perylene derivatives, pyrane derivatives and fluoranthene derivatives.

12. An organic electroluminescence device according to claim 8, wherein the substance forming a recombination site is at least one compound selected from the group consisting of styrylamine compounds, quinacridone derivatives, rubrene derivatives, coumarine derivatives, perylene derivatives, pyrane derivatives and fluoranthene derivatives.

13. An organic electroluminescence device according to claim 5, wherein a layer of a chalcogenide, a layer of a metal halide or a layer of a metal oxide is formed between the organic light emitting area and a cathode or an anode.

14. An organic electroluminescence device according to claim 6, wherein a layer of a chalcogenide, a layer of a metal halide or a layer of a metal oxide is formed between the organic light emitting layer and a cathode or an anode.

15. The anthracene derivative of claim 1, wherein X and Y each independently represent a substituted or unsubstituted trifunctional aromatic ring group having 6 to 30 carbon atoms.

16. The anthracene derivative of claim 1, wherein X and Y each independently represent a substituted or unsubstituted trifunctional heterocyclic group having 4 to 30 carbon atoms.

17. The anthracene derivative of claim 2, wherein $A^1$ to $A^4$ each independently represent a substituted or unsubstituted aryl group having 6 to 30 carbon atoms.

18. The anthracene derivative of claim 2, wherein $A^1$ to $A^4$ each independently represent a substituted or unsubstituted monovalent heterocyclic group having 4 to 30 carbon atoms.

19. The anthracene derivative of claim 3, wherein $A^1$ to $A^4$ each independently represent a substituted or unsubstituted aryl group having 6 to 30 carbon atoms.

20. The anthracene derivative of claim 3, wherein $A^1$ to $A^4$ each independently represent a substituted or unsubstituted monovalent heterocyclic group having 4 to 30 carbon atoms.

21. The anthracene derivative of claim 1, wherein each of $A^1$ to $A^4$ is a phenyl group.

22. The anthracene derivative of claim 2, wherein each of $A^1$ to $A^4$ is a phenyl group.

23. The anthracene derivative of claim 3, wherein each of $A^1$ to $A^4$ is each a phenyl group.

24. The anthracene derivative of claim 1, wherein each of $A^1$ to $A^4$ is a biphenyl group.

25. The anthracene derivative of claim 2, wherein each of $A^1$ to $A^4$ is a biphenyl group.

26. The anthracene derivative of claim 3, wherein each of $A^1$ to $A^4$ is a biphenyl group.

27. The anthracene derivative of claim 1, wherein each of $A^1$ to $A^4$ is a quinoline group.

28. The anthracene derivative of claim 2, wherein each of $A^1$ to $A^4$ is a quinoline group.

29. The anthracene derivative of claim 3, wherein each of $A^1$ to $A^4$ is a quinoline group.

30. The anthracene derivative of claim 3, selected from the group consisting of

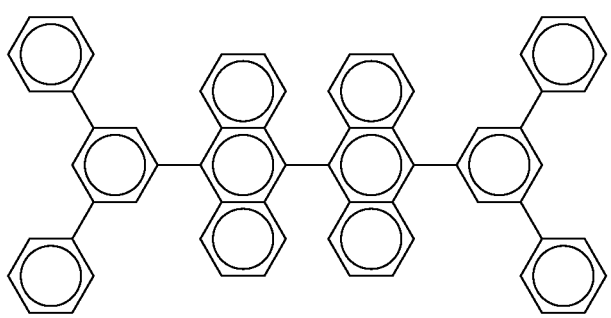

E1

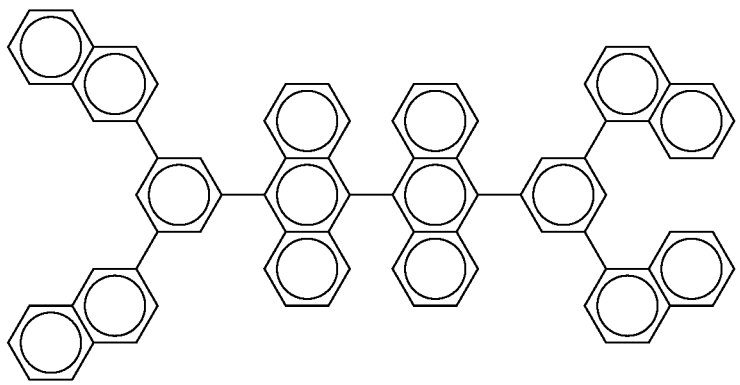

E4

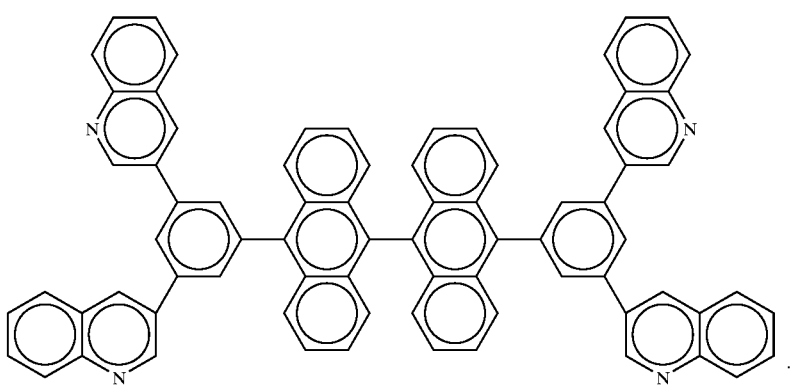

E7

* * * * *